United States Patent
Menon et al.

(10) Patent No.: US 10,052,624 B2
(45) Date of Patent: Aug. 21, 2018

(54) ZIRCONIUM PHOSPHATE AND ZIRCONIUM OXIDE RECHARGING FLOW PATHS

(71) Applicant: Medtronic, Inc., Minneapolis, MN (US)

(72) Inventors: Kanjimpuredathil Muralikrishna Menon, Bangalore (IN); Ramkumar Jeyachandran, Bangalore (IN); Kaustubh R. Patil, Bangalore (IN); Sukalyan Dutta, Bangalore (IN); Gokul Prabhu Loganathan, Bangalore (IN); David B. Lura, Maple Grove, MN (US); Bryant J. Pudil, Plymouth, MN (US); Christopher M. Hobot, Tonka Bay, MN (US)

(73) Assignee: Medtronic, Inc., Minneapolis, MN (US)

( * ) Notice: Subject to any disclaimer, the term of this patent is extended or adjusted under 35 U.S.C. 154(b) by 212 days.

(21) Appl. No.: 15/143,487

(22) Filed: Apr. 29, 2016

(65) Prior Publication Data
US 2016/0243541 A1    Aug. 25, 2016

Related U.S. Application Data

(63) Continuation-in-part of application No. 14/722,119, filed on May 26, 2015, and a continuation-in-part of
(Continued)

(51) Int. Cl.
*C22C 38/00* (2006.01)
*B01J 49/00* (2017.01)
(Continued)

(52) U.S. Cl.
CPC .......... *B01J 49/0078* (2013.01); *A61L 12/00* (2013.01); *A61M 1/169* (2013.01);
(Continued)

(58) Field of Classification Search
None
See application file for complete search history.

(56) References Cited

U.S. PATENT DOCUMENTS 3,840,835 A    11/1974    Marantz
3,850,835 A    11/1974    Marantz
(Continued)

FOREIGN PATENT DOCUMENTS

CN    1487853 A    4/2004
CN    105658326 A    6/2016
(Continued)

OTHER PUBLICATIONS

European Search Report and Supplemental Search Report in European Application No. 14865374.4 dated Jun. 12, 2017.
(Continued)

*Primary Examiner* — Richard C Gurtowski
(74) *Attorney, Agent, or Firm* — Kenneth Collier; Roger Hahn

(57) ABSTRACT

Systems and methods for recharging zirconium phosphate and zirconium oxide are provided. The systems and methods provide for recharging of the zirconium phosphate and zirconium oxide in reusable sorbent modules. The systems and methods include recharging flow paths for recharging zirconium phosphate independently or concurrently.

20 Claims, 11 Drawing Sheets

Related U.S. Application Data application No. 14/722,068, filed on May 26, 2015, now Pat. No. 9,981,245, said application No. 14/722,119 is a continuation-in-part of application No. 14/261,651, filed on Apr. 25, 2014, now Pat. No. 9,895,477, and a continuation-in-part of application No. 14/642,847, filed on Mar. 10, 2015, now Pat. No. 9,974,896, said application No. 14/722,068 is a continuation-in-part of application No. 14/261,651, filed on Apr. 25, 2014, now Pat. No. 9,895,477, and a continuation-in-part of application No. 14/642,847, filed on Mar. 10, 2015, now Pat. No. 9,974,896.

(60) Provisional application No. 61/941,672, filed on Feb. 19, 2014, provisional application No. 61/909,372, filed on Nov. 26, 2013, provisional application No. 62/016,613, filed on Jun. 24, 2014, provisional application No. 62/077,159, filed on Nov. 7, 2014.

(51) Int. Cl.
| | | |
|---|---|---|
| *A61L 12/00* | (2006.01) | |
| *B01J 41/10* | (2006.01) | |
| *B01J 39/12* | (2006.01) | |
| *A61M 1/16* | (2006.01) | |
| *B01J 20/34* | (2006.01) | |
| *B01J 20/02* | (2006.01) | |
| *B01J 39/09* | (2017.01) | |
| *B01J 49/60* | (2017.01) | |

(52) U.S. Cl.
CPC ........ *A61M 1/1696* (2013.01); *B01J 20/0211* (2013.01); *B01J 20/3475* (2013.01); *B01J 20/3483* (2013.01); *B01J 39/09* (2017.01); *B01J 39/12* (2013.01); *B01J 41/10* (2013.01); *B01J 49/60* (2017.01); *A61M 2205/0205* (2013.01); *A61M 2205/3317* (2013.01); *A61M 2205/3324* (2013.01); *A61M 2205/3331* (2013.01); *A61M 2205/3334* (2013.01); *A61M 2205/3368* (2013.01); *A61M 2205/3372* (2013.01)

(56) References Cited

U.S. PATENT DOCUMENTS

| | | | |
|---|---|---|---|
| 4,192,748 | A | 3/1980 | Hyden |
| 4,687,582 | A | 8/1987 | Dixon |
| 6,579,460 | B1 | 6/2003 | Willis |
| 2002/0112609 | A1 | 8/2002 | Wong |
| 2003/0097086 | A1 | 5/2003 | Gura |
| 2005/0056592 | A1 | 3/2005 | Braunger |
| 2005/0274658 | A1 | 12/2005 | Rosenbaum |
| 2006/0241543 | A1 | 10/2006 | Gura |
| 2008/0011664 | A1 | 1/2008 | Karoor |
| 2008/0241031 | A1 | 10/2008 | Li |
| 2009/0101552 | A1 | 4/2009 | Fulkerson |
| 2009/0282980 | A1 | 11/2009 | Gura |
| 2010/0004588 | A1 | 1/2010 | Yeh |
| 2010/0078387 | A1 | 4/2010 | Wong |
| 2010/0312172 | A1 | 12/2010 | Hoffman |
| 2011/0017665 | A1 | 1/2011 | Updyke |
| 2011/0048949 | A1 | 3/2011 | Ding |
| 2011/0171713 | A1 | 7/2011 | Bluchel |
| 2011/0272352 | A1 | 11/2011 | Braig |
| 2011/0297593 | A1 | 12/2011 | Kelly |
| 2012/0273354 | A1 | 11/2012 | Orhan et al. |
| 2013/0199998 | A1 | 8/2013 | Kelly |
| 2013/0213890 | A1 | 8/2013 | Kelly |
| 2014/0158588 | A1 | 6/2014 | Pudil |
| 2014/0158623 | A1 | 6/2014 | Pudil |
| 2015/0108069 | A1 | 4/2015 | Merchant |
| 2015/0251161 | A1 | 9/2015 | Pudil |
| 2015/0251162 | A1 | 9/2015 | Pudil |
| 2015/0367055 | A1 | 12/2015 | Pudil |

FOREIGN PATENT DOCUMENTS

| | | |
|---|---|---|
| EP | 2446908 | 5/2012 |
| JP | S5070281 A | 6/1975 |
| JP | S51-55193 | 5/1976 |
| JP | S51-131393 | 11/1976 |
| JP | S61164562 | 7/1986 |
| JP | 2981573 | 11/1999 |
| JP | 2005511250 | 4/2005 |
| JP | 2007-44602 A | 2/2007 |
| JP | 200744602 | 2/2007 |
| JP | 200744602 A | 2/2007 |
| JP | 201352987 | 1/2013 |
| WO | WO 2011/017215 | 2/2011 |
| WO | WO 2013/019994 | 2/2013 |
| WO | WO 2013-025957 | 2/2013 |
| WO | WO 2013-028809 | 2/2013 |
| WO | WO 2013019179 | 2/2013 |
| WO | 2013101888 | 7/2013 |
| WO | WO 2013/103607 | 7/2013 |
| WO | 2015060914 | 4/2015 |
| WO | 2015199765 | 12/2015 |
| WO | 2015199863 | 12/2015 |
| WO | 2015199864 | 12/2015 |

OTHER PUBLICATIONS

PCT/US2015/019901 International Search Report and Written Opinion dated Jun. 5, 2015.
PCT/US2015/032492 International Search Report dated Nov. 19, 2015.
PCT/US2015/032492 Written Opinion dated Nov. 19, 2015.
Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
PCT/US2016/030320 Written Opinion dated Jul. 27, 2016.
Office Action in App. No. AU 2015280604 dated Apr. 8, 2016.
Wester et al., A regenerable postassium and phosphate sorbent system to enhance dialysis efficacy and device portability: an in vitro study Nephrol Dial Transplant (2013) 28: 2364-2371 Jul. 3, 2013.
John Wm Agar: "Review: Understanding sorbent dialysis systems," Nephrology, vol. 15, No. 4, Jun. 1, 2010, pp. 406-411.
Office Action in App. No. JP 2016-515476 dated Dec. 26, 2016.
Japanese Patent Publication No. S50-70281A.
Japanese Patent Publication No. 2007-44602A.
PCT/US2015/032494 Written Opinion dated Nov. 19, 2015.
PCT/US2015/032494 International Search Report dated Nov. 19, 2015.
PCT/US2015/019901 International Preliminary Report on Patentability dated May 27, 2016.
PCT/US2015/019901 Written Opinion dated May 27, 2016.
PCT/US2015/019901 Written Opinion dated Jun. 5, 2015.
PCT/US2015/019901 International Search Report dated Jun. 5, 2015.
PCT/US2015/032485 International Preliminary Report on Patentability dated May 11, 2016.
PCT/US20115/032485 International Preliminary Report on Patentability dated May 11, 2016.
PCT/US2016/030304 International Search Report dated Jul. 27, 2016.
PCT/US2016/030304 Written Opinion dated Jul. 27, 2016.
PCT/US2016/030312 Written Opinion dated Jul. 28, 2016.
PCT/US2016/030312 International Search Report dated Jul. 28, 2016.
PCT/US2016/030319 Written Opinion dated Jul. 27, 2016.
PCT/US2016/030319 International Search Report dated Jul. 27, 2016.
PCT/US2016/030320 International Search Report dated Jul. 28, 2016.

(56) References Cited

OTHER PUBLICATIONS

PCT/US2016/030320 Written Opinion dated Jul. 28, 2016.
PCT/US2015/032485 Written Opinion dated May 9, 2016.
PCT/US2015/032485 Written Opinion dated Oct. 16, 2015.
PCT/US2016/030320 International Preliminary Report on Patentability, dated Apr. 20, 2017.
PCT/US2015/032494 International Preliminary Report on Patentablity dated Dec. 27, 2016.
European Search Report for App. No. 15812081.6, dated Mar. 8, 2018.
PCT/US2016/030319_IPRP.
[NPL622] PCT/US2015/032485 Written Opinion dated Oct. 16, 2015.
[NPL696] PCT/US2015/032485 Written Opinion dated May 9, 2016.
European Search Report for EP App. No. 15811326.6, dated Feb. 12, 2018.
European Search Report for EP App. No. 15812413.1, dated Feb. 2, 2018.
Search Report in EP App. No. 15752771, dated Nov. 22, 2017.
[NPL721] PCT/US2015/019901 International Preliminary Report on Patentability dated May 27, 2016.
[NPL720] PCT/US2015/019901 International Search Report and Written Opinion dated Jun. 5, 2015.
[NPL756] European Search Report and Supplemental Search Report in European Application No. 14865374.4 dated Jun. 12, 2017.
[NPL722] PCT/US2015/032494 International Preliminary Report on Patentablity dated Dec. 27, 2016.
[NPL10] Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
[NPL591] PCT/US2016/030320 Written Opinion dated Jul. 27, 2016.
[NPL603] Japanese Patent Publication No. S50-70281A.
[NPL602] Office Action in App. No. JP 2016-515476 dated Dec. 26, 2016.
[NPL605] PCT/US2015/032494 Written Opinion dated Nov. 19, 2015.
[NPL606] PCT/US2015/032494 International Search Report dated Nov. 19, 2015.
[NPL608] PCT/US2015/019901 Written Opinion dated May 27, 2016.
[NPL609] PCT/US2015/019901 Written Opinion dated Jun. 5, 2015.
[NPL611] PCT/US2015/032485 International Preliminary Report on Patentability dated May 11, 2016.
[NPL612] PCT/US2015/032485 International Preliminary Report on Patentability dated May 11, 2016.
[NPL613] PCT/US20115/032485 International Preliminary Report on Patentability dated May 11, 2016.
[NPL615] PCT/US2016/030304 Written Opinion dated Jul. 27, 2016.
[NPL616] PCT/US2016/030312 Written Opinion dated Jul. 28, 2016.
[NPL617] PCT/US2016/030312 International Search Report dated Jul. 28, 2016.
[NPL618] PCT/US2016/030319 International Search Report dated Jul. 27, 2016.
[NPL619] PCT/US2016/030319 Written Opinion dated Jul. 27, 2016.
[NPL607] PCT/US2015/019901 International Preliminary Report on Patentability dated May 27, 2016.
[NPL610] PCT/US2015/019901 International Search Report dated Jun. 5, 2015.
[NPL621] PCT/US2016/030320 International Search Report dated Jul. 28, 2016.
[NPL623] PCT/US2015/032485 Written Opinion dated Oct. 16, 2016.
[NPL634] PCT/US2016/030320 International Preliminary Report on Patentability, dated Apr. 20, 2017.
[NPL6] PCT/US2015/032492 Written Opinion dated Nov. 19, 2015.
[NPL2] PCT/US2015/032492 International Search Report dated Nov. 19, 2015.
[NPL584] Office Action in App. No. AU 2015280604 dated Apr. 8, 2016.
[NPL601] Wester et al., A regenerable postassium and phosphate sorbent system to enhance dialysis efficacy and device portability: an in vitro study Nephrol Dial Transplant (2013) 28: 2364-2371 Jul. 3, 2013.
[NPL494] John Wm Agar: Review: Understanding sorbent dialysis systems, Nephrology, vol. 15, No. 4, Jun. 1, 2010, pp. 406-411.
[NPL614] PCT/US2016/030304 International Search Report dated Jul. 27, 2016.
[NPL620] PCT/US2016/030320 Written Opinion dated Jul. 28, 2016.
[NPL626] PCT/US2015/032485 International Search Report and Written Opinion dated Oct. 16, 2015.
[NPL3] PCT/US2015/019901 International Search Report and Written Opinion dated Jun. 5, 2015.
PCT/US2016/030304_IPRP.
Office Action in Japanese Application No. 2016/553344, dated Apr. 24, 2018.

ued States Patent 10,052,624 B2

ZIRCONIUM PHOSPHATE AND ZIRCONIUM OXIDE RECHARGING FLOW PATHS

FIELD OF THE INVENTION

The invention relates to systems and methods for recharging zirconium phosphate and/or zirconium oxide used in sorbent dialysis. The systems and methods include rechargers, flow paths, related components, and control logic for simultaneously or independently recharging reusable modules containing zirconium phosphate or zirconium oxide.

BACKGROUND

Zirconium phosphate and zirconium oxide are used in sorbent dialysis to remove waste and unwanted solutes from spent dialysate. Generally, zirconium phosphate removes ammonium, potassium, calcium, and magnesium ions from dialysate while the zirconium oxide removes anions such as phosphate or fluoride ions. Both materials are usually packaged together in a cartridge of some type or packed in separate cartridges. Usually, sorbent cartridges are discarded and replaced after use. The discarded sorbent cartridges are broken down and the individual materials separated from each other. Because zirconium phosphate and zirconium oxide are expensive and rechargeable, sorbent re-processers treat the recovered zirconium phosphate and zirconium oxide with a series of chemical solutions. The recycling process requires transporting the materials to reprocessing facilities and involves laborious recycling steps in addition to recharging the sorbent materials. Further, the sorbent material cannot be immediately reused, and must be added to a new sorbent cartridge and repackaged for sale. Safe disposal of the chemical waste from solutions used to recharge the materials may also require additional steps such as neutralizing the recharging solutions. Conventional methods drive up costs and infrastructure requirements, and increase complexity and waste.

Hence, there is a need for systems and methods that can quickly and effectively recharge sorbent materials without the need to remove the spent sorbent materials from the sorbent cartridge or sorbent modules. There is further a need for systems and methods that can quickly and effectively recharge different sorbent materials in a single recharging system. There is also a need for a system that can take advantage of the unique solutions necessary to recharge both zirconium oxide and zirconium phosphate to allow for automatic neutralization of the recharging solutions allowing safe disposal without additional treatment. There is further a need for systems and methods that can provide inline mixing of chemicals, reducing the volumes of chemicals needed.

SUMMARY OF THE INVENTION

The invention is drawn to a recharging flow path for recharging zirconium oxide and zirconium phosphate. In any embodiment, the recharging flow path can have a zirconium phosphate recharging flow path and a zirconium oxide recharging flow path. The zirconium phosphate recharging flow path can have (i) a water source, a disinfectant source, and a brine source; (ii) a zirconium phosphate module inlet and a zirconium phosphate module outlet; wherein the zirconium phosphate module inlet and the zirconium phosphate module outlet are fluidly connectable to a sorbent module containing zirconium phosphate; (iii) at least one zirconium phosphate pump for pumping fluid from the water source, the disinfectant source, and the brine source to the zirconium phosphate module inlet; and (iv) a zirconium phosphate effluent line fluidly connected to the zirconium phosphate module outlet.

In any embodiment of the first aspect of the invention, the zirconium oxide recharging flow path has (i) the water source, the disinfectant source, and a base source; (ii) a zirconium oxide module inlet and a zirconium oxide module outlet; wherein the zirconium oxide module inlet and the zirconium oxide module outlet are fluidly connectable to a sorbent module containing zirconium oxide; (iii) at least one zirconium oxide pump for pumping fluid from the water source, the disinfectant source, and the base source to the zirconium oxide module inlet; and a zirconium oxide effluent line fluidly connected to the zirconium oxide module outlet.

In any embodiment, the zirconium phosphate recharging flow path or zirconium oxide recharging flow path can operate simultaneously or independently.

In any embodiment, either or both of the zirconium phosphate recharging flow path and the zirconium oxide recharging flow path can have at least two pumps.

In any embodiment, the zirconium phosphate effluent line can be fluidly connected to the zirconium oxide effluent line at an effluent line junction.

In any embodiment, the recharging flow path can have a static mixer downstream of the effluent line junction.

In any embodiment, the recharging flow path can have a drain line fluidly connected to the junction, wherein the drain line is fluidly connected to a drain downstream of the static mixer.

In any embodiment, the zirconium phosphate effluent line is fluidly connected to a first waste reservoir; and the zirconium oxide effluent line is fluidly connected to a second waste reservoir.

In any embodiment, a waste reservoir can be fluidly connected to the zirconium phosphate effluent line and zirconium oxide effluent line.

In any embodiment, the recharging flow path can have either or both of a heater positioned in the zirconium phosphate recharging flow path upstream of the zirconium phosphate module inlet or a heater positioned in the zirconium oxide recharging flow path upstream of the zirconium oxide module inlet.

In any embodiment, the recharging flow path can have a heat exchanger; wherein the heat exchanger has at least a first chamber and a second chamber; and wherein either or both of: the first chamber is positioned in the zirconium phosphate recharging flow path upstream of the heater; and wherein the second chamber is positioned in the zirconium phosphate effluent line; or the first chamber is positioned in the zirconium oxide recharging flow path upstream of the heater; and wherein the second chamber is positioned in the zirconium oxide effluent line.

In any embodiment, the recharging flow path can have a heater positioned in the zirconium oxide recharging flow path upstream of the zirconium oxide module inlet.

In any embodiment, the recharging flow path can have a heat exchanger; wherein the heat exchanger has at least a first chamber and a second chamber; wherein the first chamber is positioned in the zirconium oxide recharging flow path upstream of the heater; and wherein the second chamber is positioned in the zirconium oxide effluent line.

In any embodiment, either or both of the zirconium phosphate recharging flow path and zirconium oxide recharging flow path can have a rinse loop; wherein the rinse loop is fluidly connected to a first valve positioned in the zirconium phosphate recharging flow path upstream of the heater and heat exchanger; and wherein the rinse loop is fluidly connected to a second valve positioned in the zirconium phosphate recharging flow path downstream of the heater and heat exchanger and upstream of the zirconium phosphate module inlet; or wherein the rinse loop is fluidly connected to a first valve positioned in the zirconium oxide recharging flow path upstream of the heater and heat exchanger and a second valve positioned in the zirconium oxide recharging flow path downstream of the heater and heat exchanger and upstream of the zirconium oxide module inlet.

In any embodiment, the zirconium oxide recharging flow path can have a rinse loop; wherein the rinse loop is fluidly connected to a first valve positioned in the zirconium oxide recharging flow path upstream of the heater and heat exchanger; and wherein the rinse loop is fluidly connected to a second valve positioned in the zirconium oxide recharging flow path downstream of the heater and heat exchanger and upstream of the zirconium oxide module inlet.

In any embodiment, the recharging flow path can have either or both of a zirconium phosphate bypass line and a zirconium oxide bypass line; wherein the zirconium phosphate bypass line fluidly connects the zirconium phosphate recharging flow path at a position upstream of the zirconium phosphate module inlet to the zirconium phosphate effluent line; and wherein the zirconium oxide bypass line fluidly connects the zirconium oxide recharging flow path at a position upstream of the zirconium oxide module inlet to the zirconium oxide effluent line.

In any embodiment, the recharging flow path can have a first sensor positioned in the zirconium phosphate effluent line and a second sensor positioned in the zirconium oxide effluent line. The sensors can be conductivity sensors, pH sensors, or temperature sensors.

In any embodiment, the zirconium phosphate recharging flow path can have a first sensor, and the zirconium oxide recharging flow path can have a second sensor.

In any embodiment, the at least one zirconium phosphate pump can include a first zirconium phosphate pump and a second zirconium phosphate pump; the water source being fluidly connected to the zirconium phosphate recharging flow path through a first valve; either or both of the disinfectant source and brine source being fluidly connected to the zirconium phosphate recharging flow path through a second valve; the first zirconium phosphate pump being positioned in the zirconium phosphate recharging flow path downstream of the first valve and upstream of a static mixer; and the second zirconium phosphate pump being positioned in the zirconium phosphate recharging flow path downstream of the second valve and upstream of the static mixer.

In any embodiment, the first sensor can be positioned downstream of the static mixer.

In any embodiment, the at least one zirconium oxide pump can include a first zirconium oxide pump and a second zirconium oxide pump; the water source can be fluidly connected to the zirconium oxide recharging flow path through a first valve; the disinfectant source and the base source can be fluidly connected to the zirconium oxide recharging flow path through a second valve; the first zirconium oxide pump can be positioned in the zirconium oxide recharging flow path downstream of the first valve and upstream of a static mixer; and wherein the second zirconium oxide pump can be positioned in the zirconium oxide recharging flow path downstream of the second valve and upstream of the static mixer; wherein the second sensor is positioned downstream of the static mixer.

In any embodiment, the second sensor can be positioned downstream of the static mixer. In any embodiment, at least one of the water source, disinfectant source, brine source, and base source can be external to a recharger housing.

In any embodiment, at least one of the water source, disinfectant source, brine source, and base source can be fluidly connected to a second recharging flow path.

In any embodiment, the recharging flow path can have at least one conductivity sensor positioned in the zirconium phosphate recharging flow path upstream of the zirconium phosphate module inlet, and at least a second conductivity sensor positioned in the zirconium oxide recharging flow path upstream of the zirconium oxide module inlet.

In any embodiment, the recharging flow path can have at least one of a pressure sensor and flow sensor fluidly positioned in the zirconium phosphate recharging flow path, and at least one of a pressure sensor and flow sensor positioned in the zirconium oxide recharging flow path. The pressure sensors and flow sensors can be upstream of the zirconium oxide module inlet and the zirconium phosphate module inlet.

In any embodiment, the disinfectant source can be a peracetic acid solution having a concentration in a range between 0.5% and 2% of peracetic acid in water and the base source can be a sodium hydroxide solution having a concentration greater than 2% of sodium hydroxide in water.

The features disclosed as being part of the invention can be in the invention, either alone or in combination.

DETAILED DESCRIPTION OF THE INVENTION

Figure 1A:
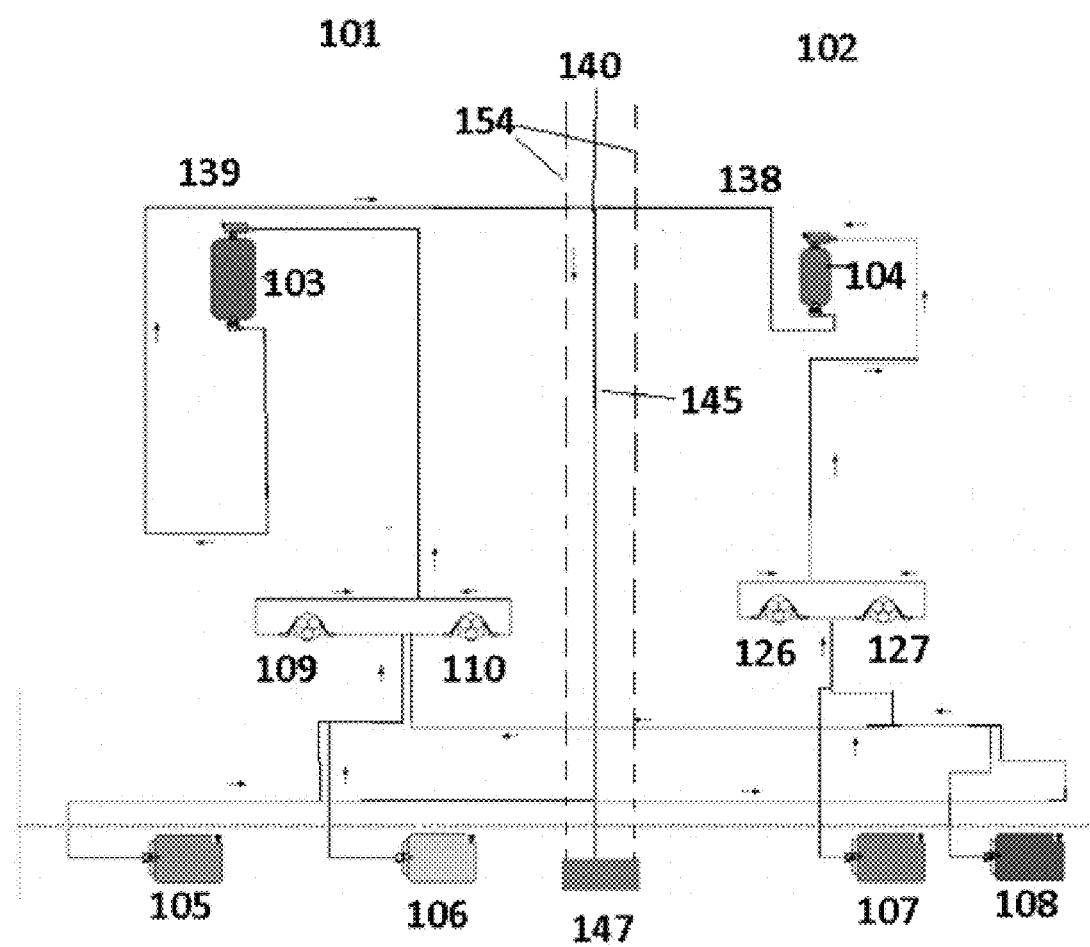
FIG. 1A shows a recharging flow path for recharging zirconium phosphate and zirconium oxide.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

A "base source" is a fluid or concentrate source from which a basic solution can be obtained.

A "brine source" is a fluid or concentrate source from which a brine solution can be obtained. As used herein, a brine solution can refer to any solution comprising acids, bases and/or salts.

A "chamber" is a portion of a component or container physically separated from another portion of the component or container.

A "common reservoir" can be a container for collecting fluid of any type from one or more fluid sources including fluid lines or other reservoirs. The "common reservoir" can for example, store used or waste fluids.

The term "comprising" includes, but is not limited to, whatever follows the word "comprising." Use of the term indicates the listed elements are required or mandatory but that other elements are optional and may be present.

A "conductivity sensor" is a sensor configured to measure the conductivity of a fluid.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "contain," "containing," or "contained" as used herein means to keep a material within a specific place. "Contain" can refer to materials placed within a component, absorbed onto a component, bound to a component, or any other method of keeping the material in a specific place.

The terms "conveying," "conveyed," or to "convey" refers to moving a fluid.

A "disinfectant source" is a fluid or concentrate source from which a disinfectant solution can be obtained. The disinfectant solution can be an acidic solution, such as a peracetic acid solution, or any other solution capable of disinfecting reusable sorbent modules.

The term "downstream" refers to a position of a first component in a flow path relative to a second component wherein fluid will pass by the second component prior to the first component during normal operation. The first component can be said to be "downstream" of the second component, while the second component is "upstream" of the first component.

A "drain" is a fluid line through which fluids may be disposed.

A "drain line" is a fluid line through which used or waste fluid may flow for disposal. The drain line can be connected to a drain, or to a container or reservoir for later disposal of the fluid.

An "effluent line" is a fluid passageway, tube, line, or path of any kind into which fluid exiting a container, module, or component will flow.

An "effluent line junction" is a location where at least two effluent lines are connected to each other, with or without a valve.

The term "external" refers to a component, module, or fluid line being situated or positioned outside of a casing or rigid structure.

A "flow sensor" is a device capable of measuring an amount or rate of fluid moving past or through a location.

A "fluid" is a liquid substance optionally having a combination of gas and liquid phases in the fluid. Notably, a liquid, as used herein, can therefore also have a mixture of gas and liquid phases of matter.

The term "fluidly connectable," "fluidly connect," "for fluid connection," and the like, refer to the ability of providing for the passage of fluid or gas or mixtures thereof, from one point to another point. The two points can be within or between any one or more of compartments, modules, systems, components, and rechargers, all of any type. The connection can optionally be disconnected and then reconnected.

A "fluid connector," "fluid connection," and the like describe a connection between two components wherein fluid, gas, or a combination thereof, can flow from one component, through a connector or a component for connection, to another component. The connector provides for a fluid connection in its broadest sense and can include any type of tubing, fluid or gas passageway, or conduit between any one or more components of the invention. The connection can optionally be disconnected and then reconnected.

The term "fluid line mixing" refers to mixing fluids at a location or junction wherein flow at the location of junction can, in part, mix one or more fluids.

A "heater" is a component capable of raising the temperature of a substance, container, or fluid.

A "heat exchanger" is a device comprising at least two chambers, wherein a fluid, gas, or combination thereof, can pass through one chamber, while a second fluid, gas, or combination thereof, can pass through the second chamber. Heat transfer occurs between the two chambers of the heat exchanger, such that if the fluids, gases, or combinations thereof, in opposite chambers are at different temperatures, the higher temperature fluid, gas, or combination thereof, will act to heat up the lower temperature fluid, gas, or combination thereof.

The term "mixing" generally refers to causing one or more fluids from any source to combine together. For example, "mixing" can include laminar or turbulent flow at a location in a fluid line or a junction. Another example of "mixing" can include receiving one or more fluids in a component configured to receive fluids from one or multiple sources and to mix the fluids together. Another aspect of mixing includes where one fluid is used to dissolve all or parts of a solid when the solid and fluid are brought together. Additionally, mixing can refer to the dissolution of a solid or solids with a fluid, wherein the solid or solids is dissolved in the fluid.

A "module inlet" is a connector through which a fluid, slurry, or aqueous solution can enter a sorbent module.

A "module outlet" is a connector through which a fluid, slurry, or aqueous solution can exit a sorbent module.

The term "positioned" or "position" refers to a physical location of a component or structure.

The term "pressure sensor" refers to a device for measuring the pressure of a gas or liquid in a vessel, container, or fluid line.

The term "pump" refers to any device that causes the movement of fluids, gases, or combinations thereof, by applying suction or pressure.

A "sorbent recharger", or generally referred to as a "recharger" herein, is an apparatus designed to recharge at least one sorbent material.

A "recharger housing" refers to a rigid casing or structure enclosing and protecting the components of the recharger flow paths and related components.

"Recharging" refers to treating a sorbent material to restore the functional capacity of the sorbent material to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged." Recharging of rechargeable sorbent materials is not the same as replenishing of a sorbent material such as urease. Notably, urease is not "recharged," but can be replenished, as defined herein.

A "recharging flow path" is a path through which fluid can travel while recharging sorbent material in a reusable sorbent module.

A "recharging solution" is a solution comprising the appropriate ions for recharging a specific sorbent material.

A "rinse loop" is a fluid pathway that connects one portion of a flow path to a second portion of a flow path and is designed to transfer fluids for rinsing a component.

The terms "sensing," "sensed," or to "sense" refer to determining one or more parameter or variable.

A "sensor" is a component capable of determining or sensing the states of one or more variables in a system.

A "sorbent cartridge module" or "sorbent module" means a discreet component of a sorbent cartridge. Multiple sorbent cartridge modules can be fitted together to form a sorbent cartridge of two, three, or more sorbent cartridge modules. In some embodiments, a single sorbent cartridge module can contain all of the necessary materials for dialysis. In such cases, the sorbent cartridge module can be a "sorbent cartridge."

A "static mixer" is a component configured to receive fluids from one or multiple sources and to mix the fluids together. The static mixer may include components that agitate the fluids to further mixing.

The term "upstream" refers to a position of a first component in a flow path relative to a second component wherein fluid will pass by the first component prior to the second component during normal operation. The first component can be said to be "upstream" of the second component, while the second component is "downstream" of the first component.

A "valve" is a device capable of directing the flow of fluid, gas, or combination thereof by opening, closing or obstructing one or more pathways to control whether the fluid, gas, or combination thereof, to travel in a path. One or more valves that accomplish a desired flow can be configured into a "valve assembly."

A "waste reservoir" is a container for collecting and storing used or waste fluids.

A "water source" is a fluid source from which water can be obtained.

A "zirconium oxide bypass line" refers to a fluid line that provides for movement of fluid between two points without passing through a zirconium oxide sorbent module.

A "zirconium oxide pump" is a pump positioned in a zirconium oxide recharging flow path A "zirconium oxide recharging flow path" is a path through which fluid can travel while recharging zirconium oxide in a reusable zirconium oxide sorbent module.

A "zirconium phosphate bypass line" refers to a fluid line that provides for movement of fluid between two points without passing through a zirconium phosphate sorbent module.

A "zirconium phosphate pump" is a pump positioned in a zirconium phosphate recharging flow path.

A "zirconium phosphate recharging flow path" is a path through which fluid can travel while recharging zirconium phosphate in a reusable zirconium phosphate sorbent module.

Flow Paths Recharging Sorbent Materials

Figure 1B:
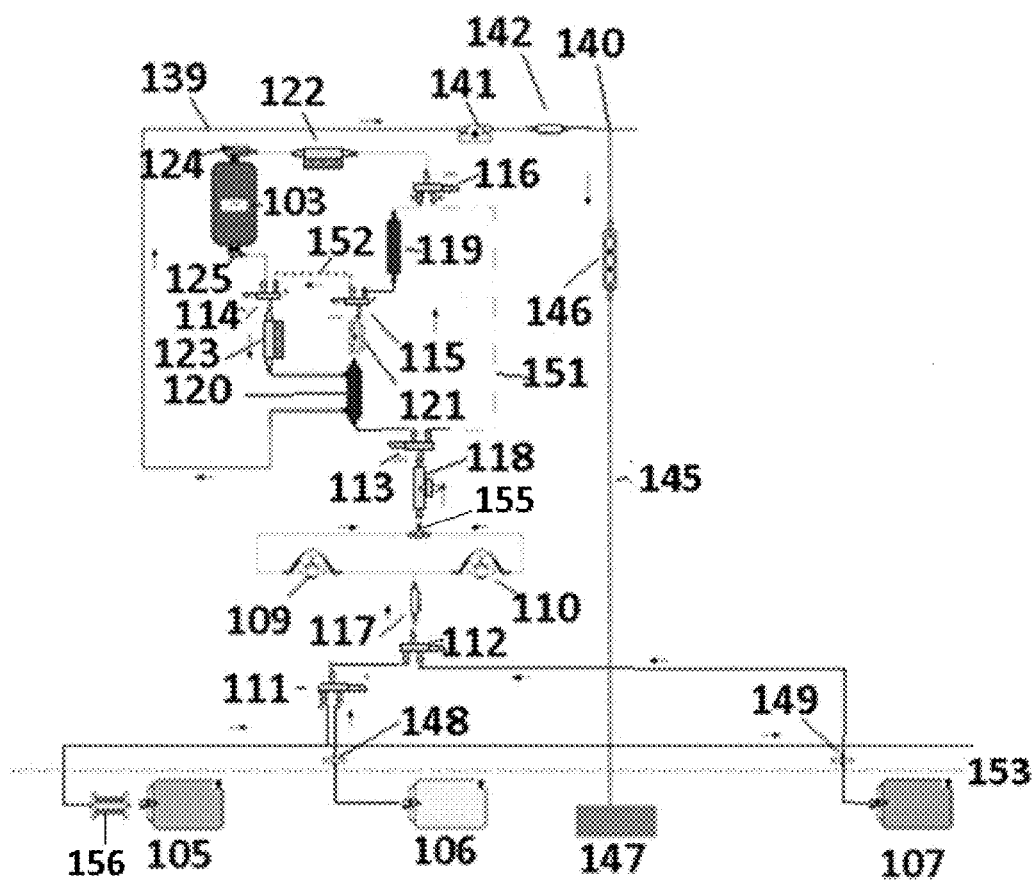
FIG. 1B shows a recharging flow path for recharging zirconium phosphate and is an exploded left side of FIG. 1A.
Figure 1C:
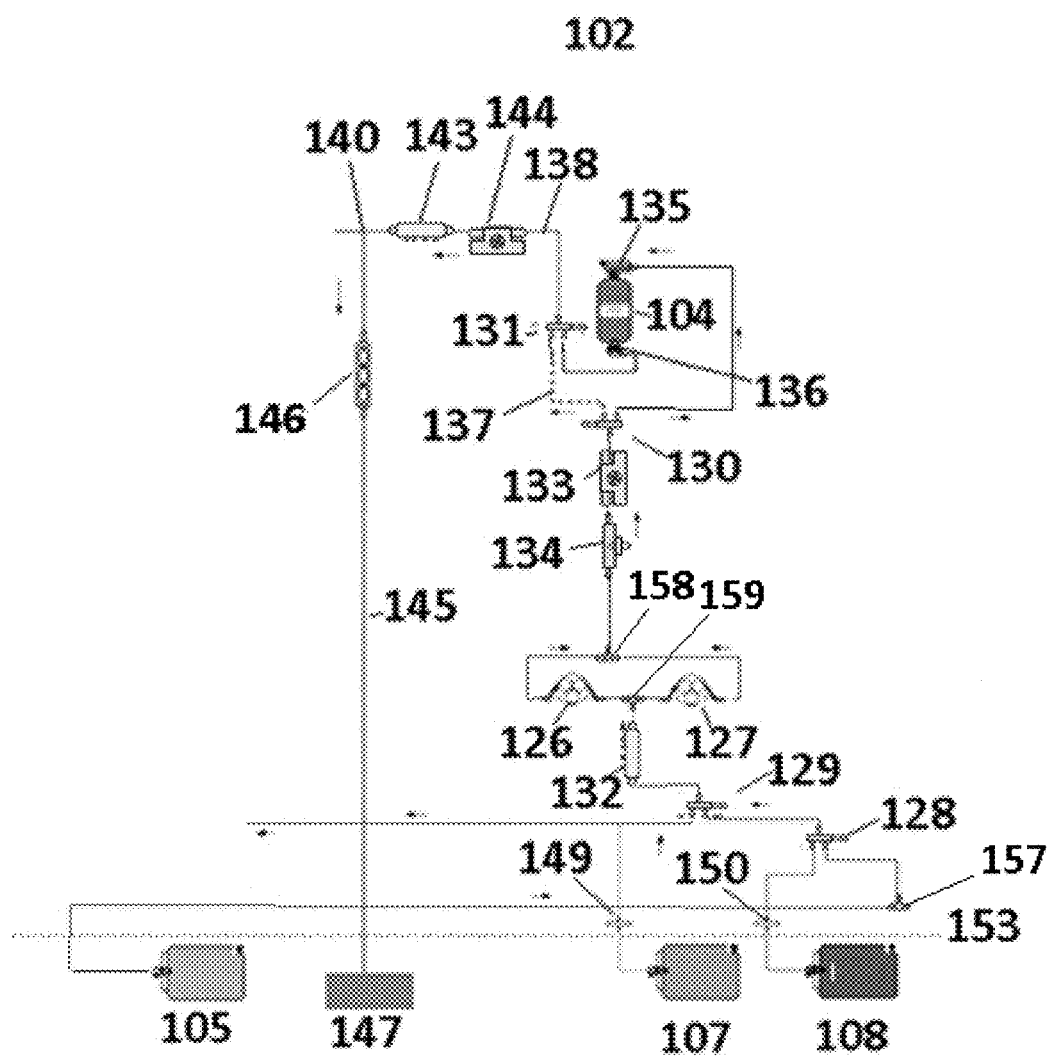
FIG. 1C shows a recharging flow path for recharging zirconium oxide and is an exploded right side of FIG. 1A.

Flow paths can be used to recharge one or more reusable sorbent modules that separately contain zirconium phosphate or zirconium oxide. The flow paths described can also recharge multiple reusable sorbent modules and neutralize effluent waste solutions for safe and easy disposal. The flow paths of the invention can be arranged as shown in FIGS. 1A-C. FIG. 1A is a generalized view of a recharging flow path, with details shown in FIGS. 1B and 1C. The recharging flow path can be divided into a zirconium phosphate recharging flow path 101 containing the zirconium phosphate module 103 and a zirconium oxide recharging flow path 102 containing zirconium oxide module 104. Details of the zirconium phosphate recharging flow path 101 on the zirconium phosphate side of line 154 are illustrated in FIG. 1B, while details of the zirconium oxide recharging flow path 102 on the zirconium oxide side of line 154 are illustrated in FIG. 1C. Although a dual cartridge recharger system is shown, single, two, three, or more multiple cartridge recharger systems are envisioned. Any one of the recharger cartridge systems can be linked together to share resources for recharging the sorbent cartridge and can be adapted for large scale use. Similarly, the linked rechargers can be scaled down as demand for recharging decreases. The modular recharging set-up having more or less rechargers based on demand can be advantageously used where required.

In FIG. 1A, a zirconium phosphate recharging flow path 101 has a water source 105, a brine source 106, a disinfectant source 107, and a base source 108. The brine source 106, disinfectant source 107, and/or base source 108 can be a column containing a dry bed of the brine, disinfectant, and/or base components. Alternatively, a powdered source of the brine, disinfectant, and/or base components can be used. The dry bed or powdered source can be dissolved with an aqueous solution. A static mixer (not shown) can mix the single line coming through the column prior to entering the zirconium phosphate module 103 or zirconium oxide module 104. Recharging the zirconium phosphate in a zirconium phosphate module 103 requires water, brine, and disinfectant. The water source 105, the brine source 106, and the disinfectant source 107 are fluidly connected to the zirconium phosphate recharging flow path 101. Similarly, recharging zirconium oxide module 104 in zirconium oxide recharging flow path 102 requires water, base, and disinfectant. The water source 105, the disinfectant source 107, and the base source 108 can be fluidly connected to the zirconium oxide recharging flow path 102. The zirconium phosphate recharging flow path 101 and zirconium oxide recharging flow path 102 can be operated simultaneously or independently. Disinfectant source 107 can contain any type of disinfectant compatible with zirconium phosphate and zirconium oxide capable of disinfecting the reusable sorbent modules. In any embodiment, the disinfectant source 107 can contain peracetic acid. In any embodiment, the peracetic acid can be a solution of between 0.5% and 2% peracetic acid in water. Alternatively, the disinfectant source 107 can contain any disinfectant compatible with zirconium phosphate and zirconium oxide, including bleach or citric acid. The brine source 106 can have an acid, a base, and a sodium salt.

During zirconium phosphate recharging, potassium, calcium, magnesium, and ammonium ions bound to the zirconium phosphate must be replaced by hydrogen and sodium ions. The final ratio of hydrogen to sodium ions on the recharged zirconium phosphate can be determined by the pH, buffer capacity, and sodium concentration of the brine solution used in the recharging process. As shown in FIG. 1B, the brine source 106 can be a mixture of sodium chloride, sodium acetate, and acetic acid. In one non-limiting brine solution, the sodium chloride concentration can be between 2.5M and 4.9M, the sodium acetate concentration can be between 0.3M and 1.1M, and acetic acid concentration can be between 0.2M and 0.8M. The water source 105 can contain any type of water, including deionized water. To recharge the zirconium phosphate in the zirconium phosphate module 103, the disinfectant from disinfectant source 107 can flow to the zirconium phosphate module 103 to disinfect the zirconium phosphate module 103. Fluid from the disinfectant source 107 can flow to valve 112 in the zirconium phosphate recharging flow path 101. Zirconium phosphate pumps 109 and 110 provide a driving force to pump the fluid through the zirconium phosphate recharging flow path 101. Use of two or more separate pumps can reduce wear on the pumps. Correspondingly, smaller pumps can be used. The two or more pumps can provide in-line mixing and intermittent pumping so at any given time, a single pump can pump fluid through the zirconium phosphate recharging flow path 101. The two pumps can be used simultaneously or independently. The two or more pumps can provide fluid line mixing of one or more separate fluid streams when used simultaneously. The two or more pumps can operate asynchronously but used concurrently. For example, a first pump can operate for a time and a second pump remain off, then the first pump shut off with the second pump turning on. Multiple pumps at various timed pumping stages are envisioned as described herein. One of skill in the art will understand that a single zirconium phosphate pump can also accomplish the described pump functions.

Zirconium phosphate pumps 109 and 110 can pump fluid from disinfectant source 107 through valve 112 and valve 113 of FIG. 1B Fluid can be pumped through three-way junction 155 to valve 116 and into zirconium phosphate module 103 through zirconium phosphate module inlet 124. The illustrated junctions combine the inlet chemicals or water pumped by the two pumps such that higher flow rates can be achieved. During filling, fluid inside zirconium phosphate module 103 can be forced through zirconium phosphate module outlet 125 and into zirconium phosphate module effluent line 139. The disinfectant can be sequestered in the zirconium phosphate module 103 to ensure disinfection. Heater 119 upstream of the zirconium phosphate module 103 can heat the disinfectant because disinfection can become more efficient at elevated temperatures. After disinfection, zirconium phosphate module 103 can be rinsed using water from water source 105. Zirconium phosphate pumps 109 and 110 can pump water from water source 105 through valves 111 and 112 to valve 113. The water can then be pumped through valves 115 and 116 through the zirconium phosphate module 103 through zirconium phosphate module inlet 124, out zirconium phosphate module outlet 125 and into zirconium phosphate module effluent line 139. Water can be pumped through the zirconium phosphate module 103 until all of the disinfectant is removed.

Fluid from brine source 106 can be pumped through the zirconium phosphate module 103 to load the zirconium phosphate module 103 with the proper ratio of sodium and hydrogen ions. Zirconium phosphate pumps 109 and 110 can pump fluid from brine source 106 to valve 111. The brine can follow the same pathway as the water through zirconium phosphate module 103 and into zirconium phosphate module effluent line 139. Heater 119 upstream of the zirconium phosphate module 103 can heat brine because recharging can become more efficient at elevated temperatures. Heat exchanger 120 can lessen the load on heater 119. One or more heat exchangers and one or more heaters can be used. The heat exchanger 120 can be fluidly connected to zirconium phosphate module effluent line 139 and to zirconium phosphate module inlet 124 upstream of heater 119. The heated fluid exiting the zirconium phosphate module 103 in zirconium phosphate module effluent line 139 can heat the incoming brine solution in heat exchanger 120. The heat exchanger 120 can have at least a first chamber and a second chamber. Fluid in the zirconium phosphate inlet lines can pass through the first chamber of the heat exchanger 120, and fluid in the zirconium phosphate effluent line 139 can pass through the second chamber of the heat exchanger 120. The increased temperature of the zirconium phosphate effluent in the second chamber can heat the fluid in the zirconium phosphate inlet lines in the first chamber. The zirconium phosphate module 103 can be rinsed again by pumping water through the zirconium phosphate module 103. A static mixer (not shown) can be positioned upstream of the zirconium phosphate module 103 and mix the solutions prior to entering the zirconium phosphate module 103.

Various sensors can be used in the zirconium phosphate module recharging flow path 101 to ensure proper concentrations and temperatures as shown in FIG. 1B. For example, conductivity sensor 117 can ensure that the incoming water contain no level of ions that may interfere with the recharging process, and that the brine solution and disinfectant solution are at a desired concentration. Conductivity sensor 142 can also be used to ensure that sufficient rinsing has occurred to remove brine and disinfectant solution. Pressure sensor 118 can monitor pressure in the zirconium phosphate inlet lines to ensure there are no occlusions or leaks and that the inlet pressures are in an acceptable range. Temperature sensor(s) 122 can ensure that the brine solution is at the proper temperature before entering zirconium phosphate module 103 and to control heater 119. Temperature sensor 123 can be placed in zirconium phosphate module effluent line 139 to monitor the temperature of the effluent which can be controlled by heat exchanger 120 and heater 119. A flow sensor 121 can monitor the flow rates of the fluids in the zirconium phosphate recharging flow path 101 and control zirconium phosphate pumps 109 and 110. One of skill in the art will understand that alternative arrangements of sensors can be used in FIG. 1B and that one or more additional sensors can be added. Further, the sensors can be placed at any appropriate position in the zirconium phosphate recharging flow path 101 to determine fluid parameters at various locations throughout the zirconium phosphate recharging flow path 101.

Zirconium phosphate bypass line 152 fluidly connects valve 115 to valve 114 in the zirconium phosphate effluent line 139. Valves 115 and 116 can be controlled to direct fluid through the zirconium phosphate bypass line 152 and into zirconium phosphate effluent line 139. The dual flow path aspect of the recharging flow path depicted in FIG. 1A can neutralize the effluent from both the zirconium phosphate module 103 and zirconium oxide module 104 by mixing the acidic effluent from the zirconium phosphate module 103 with the basic effluent from zirconium oxide module 104. If only zirconium oxide module 104 is being recharged using the flow path of FIG. 1C, the zirconium phosphate bypass line 152 can be utilized to direct fluid from the brine source 106 to the zirconium phosphate effluent line 139 to neutralize the zirconium oxide effluent without the need to simultaneously recharge a zirconium phosphate module 103. Similarly, bypass line 152 can directly connect the zirconium phosphate module inlet 124 to zirconium phosphate module outlet 125. The zirconium phosphate recharging flow path 101 can include a rinse loop 151 to fluidly connect valve 113 upstream of the heater 119 and heat exchanger 120 to valve 116, bypassing heater 119 and heat exchanger 120. The rinse loop 151 can rinse brine solution from the zirconium phosphate module 103. By bypassing heater 119 and heat exchanger 120 through rinse loop 151, the zirconium phosphate module 103 can be cooled faster.

To recharge the zirconium oxide module 104 of FIG. 1C disinfectant from disinfectant source 107 can be first pumped to the zirconium oxide module 104 to disinfect the zirconium oxide module 104. Fluid from the disinfectant source 107 can be pumped to valve 129 in the zirconium oxide recharging flow path 102. Zirconium oxide pumps 126 and 127 can pump fluid through the zirconium oxide recharging flow path 102. As described, a single zirconium oxide pump can be used as an alternative to the dual pump system in FIG. 1A. Also, two or more zirconium oxide pump are contemplated. The two or more zirconium oxide pumps can provide fluid line mixing of one or more separate fluid streams when used simultaneously. The two or more zirconium oxide pumps of FIG. 1C can be asynchronous but used concurrently. For example, a first pump can operate for a time and a second pump remain off, then the first pump shut off with the second pump turning on. Multiple pumps at various timed pumping stages are envisioned as described herein. Zirconium oxide pumps 126 and 127 pump fluid from disinfectant source 107 through valve 129 to valve 130. The fluid flows to the zirconium oxide module 104 through zirconium oxide module inlet 135. During filling, fluid inside zirconium oxide module 104 can flow through zirconium oxide module outlet 136 and into zirconium oxide module effluent line 138. The disinfectant can be sequestered in zirconium oxide module 104 to ensure disinfection. The zirconium oxide module 104 can then be flushed with water from water source 105 after disinfection is completed. Zirconium oxide pumps 126 and 127 can pump water from water source 105 through valves 128 and 129 and junction 157 to valve 130. The fluid passes through junctions 158 and 159 to reach valve 130. The water can then be pumped to zirconium oxide module 104 through zirconium oxide module inlet 135 and out zirconium oxide module outlet 136 and into zirconium oxide module effluent line 138. The zirconium oxide module 104 can be flushed with any volume of water required to ensure that the disinfectant is completely removed.

In FIG. 1C, zirconium oxide pumps 126 and 127 can pump fluid from base source 108 through valve 128 to zirconium oxide module 104. The base source 108 can contain hydroxide ions to recharge zirconium oxide module 104. The hydroxide ions can flow through zirconium oxide module 104 and into zirconium oxide module effluent line 138. The base source 108 can be any suitable basic solution capable of replacing phosphate and other anions bound to the zirconium oxide with hydroxide ions. The hydroxide base can be any suitable base such as sodium hydroxide. One non-limiting example is sodium hydroxide having a concentration between 0.5M and 2.0M. Another non-limiting example is sodium hydroxide having a concentration at 90% or greater than 2% of the concentration of the recharging solution. A final rinse of the zirconium oxide module 104 can be performed by pumping water through the zirconium oxide recharging flow path 102 and zirconium oxide module 104. Zirconium oxide recharging flow path 102 can also have a zirconium oxide bypass line 137 fluidly connecting valve 130 in the zirconium oxide inlet line to valve 131 in the zirconium oxide effluent line 138. Valves 130 and 131 can direct fluid through the zirconium oxide bypass line 137 and into zirconium oxide effluent line 138. Zirconium oxide bypass line 137 can convey fluid directly from the base source 108 to the zirconium oxide effluent line 138 to neutralize the zirconium phosphate effluent without the need to simultaneously recharge a zirconium oxide module 104. Alternatively, zirconium oxide module inlet 135 can be fluidly connected to zirconium oxide module outlet 136. Multiple sensors can be included in the zirconium oxide recharging flow path 102 to monitor fluid concentration. For example, conductivity sensor 132 can be used to monitor concentrations of the zirconium oxide recharging fluid; pressure sensor 134 can be used to monitor pressure in the zirconium oxide inlet line and to detect leaks or occlusions. Flow sensor 133 can determine the flow rate of the fluid through the zirconium oxide inlet line and be used to control zirconium oxide pumps 126 and 127. A static mixer (not shown) can be positioned upstream of the zirconium oxide module 104 and mix solutions prior to entering the zirconium oxide module 104. A heater and heat exchanger (not shown) can be positioned in the zirconium oxide recharging flow path 102 to heat fluids prior to entering zirconium oxide module 104. Heating fluid in the zirconium oxide recharging flow path 102 can reduce recharging times and allow disinfection with a base solution, such as sodium hydroxide. Heating the fluid also allows for reduced disinfection time with a disinfectant source. A zirconium oxide rinse loop (not shown) can also be included to bypass the heater and heat exchanger during flushing.

Effluent from zirconium phosphate recharging flow path 101 can neutralize, either completely or in part, the effluent from zirconium oxide recharging flow path 102, and vice versa. Zirconium phosphate effluent line 139 can be fluidly connected to zirconium oxide effluent line 138 at an effluent line junction 140 joining drain line 145, which fluidly connects to drain 147. Static mixer 146 can be used at or downstream of the effluent line junction 140 to mix zirconium phosphate effluent with zirconium oxide effluent.

Zirconium phosphate effluent line 139 and zirconium oxide effluent line 138 of FIG. 1A can be connected to a common reservoir for storage and disposal of the combined effluent. The common reservoir receives and collects the zirconium phosphate and zirconium oxide effluents together. The collected effluents can be drained after appropriate volumes of each effluent have been added to achieve neutralization. A common reservoir can allow for neutralization of the zirconium phosphate and zirconium oxide effluents without synchronizing the recharging processes. A single common reservoir could also be sized to support multiple rechargers.

Alternatively, the two fluid streams may be mixed through fluid line mixing at the effluent line junction 140. Flow sensor 141 and conductivity sensor 142 can be placed in zirconium phosphate effluent line 139 to measure the flow rate and composition of the zirconium phosphate effluent. Flow sensor 144 and conductivity sensor 143 can be positioned in the zirconium oxide effluent line 138 to measure the wash and composition of the zirconium oxide effluent. Data from flow sensors 141 and 144 and conductivity sensors 142 and 143 can determine if the combined effluent in drain line 145 is safe for disposal into a drain. One non-limiting example of safe is an effluent having a pH in the range of 5.-9. Either zirconium phosphate effluent line 139 or zirconium oxide effluent line 138 can be connected simultaneously or independently to a waste reservoir (not shown) for disposal. Additional pH or conductivity sensors can be positioned downstream of the static mixer 146 to monitor and ensure safe disposal. Drain line 145 can also be connected to a common waste reservoir for storage and disposal of effluent. The common reservoir receives and collects the zirconium phosphate and zirconium oxide effluents together. The collected effluents can be drained after appropriate volumes of each effluent have been added to achieve neutralization. A common waste reservoir advantageously allows for neutralization of the zirconium phosphate and zirconium oxide effluents without synchronizing the recharging processes. Static mixer 146 may be unnecessary when a common reservoir is used.

Brine source 106, disinfectant source 107, and base source 108 can have filter 148, filter 149, and filter 150, respectively to remove particulate matter. The one or more filters can remove particulate matter before fluid enters the zirconium oxide recharging flow path 102 or zirconium oxide recharging flow path 101. Water source 105 can have microbial filter 156 to remove microbes from the water before entering the flow paths. In FIG. 1C, the dashed line 153 represents a recharger housing. The fluid sources can be external to the recharger housing and fluidly connected to the lines located inside of the recharger housing. Alternatively, the fluid sources described can instead be housed within the recharger.

During recharging, fluid can be passed through the zirconium phosphate module 103 and/or the zirconium oxide module 104 opposite to a flow direction used during dialysis. For example, zirconium phosphate module inlet 124 can be used as the zirconium phosphate module outlet during dialysis, and zirconium phosphate module outlet 125 can be the zirconium phosphate module inlet during dialysis in FIG. 1B. Similarly, zirconium oxide module inlet 135 can be used as the zirconium phosphate module outlet during dialysis, and zirconium oxide module outlet 136 can be used as the zirconium phosphate module inlet during dialysis. Pumping the recharging fluid through the modules in the opposite direction relative to dialysis can improve the efficiency of the recharging process.

The zirconium phosphate recharging flow path 101 or zirconium oxide recharging flow path 102 can independently recharge zirconium phosphate or zirconium oxide. For example, a single flow path fluidly connecting zirconium phosphate module 103 of FIG. 1B via valve 112 and valve 113 to each of the water source 105, brine source 106, and disinfectant source 107 can independently recharge the zirconium phosphate module 103. Similarly, a single flow path fluidly connecting zirconium oxide module 104 of FIG. 1C via valve 128 and valve 129 to each of the water source 105, disinfectant source 107, and base source 108 can independently recharge the zirconium oxide module 104.

The water source 105, brine source 106, disinfectant source 107, and base source 108 can recharge one or more reusable sorbent module of various sizes. The amount of water, brine, disinfectant, and base depends on the concentration of each of the recharging solutions, the size of the reusable sorbent modules, the amount of cations/anions removed, and the flow rate used to pass the solutions through the reusable modules. The amount of brine solution required can depend on the temperature to which the brine solution is heated. For example, a brine solution having between 2.5 M and 4.9 M sodium chloride, between 0.3 M and 1.1 M sodium acetate, and between 0.2 M and 0.8 M acetic acid at between 70° C. and 90° C. requires between 4.2-6.2 L of brine to recharge a zirconium phosphate module containing between 2 kg and 3.2 kg of zirconium phosphate loaded with 2 to 3 moles of ammonium, calcium, magnesium and potassium. The brine solution should have a volume of at least between 4.2 and 6.2 L and delivered at a flow rate of between 100 and 300 mL/min. A single brine source can be connected to multiple rechargers, or can recharge multiple zirconium phosphate sorbent modules in a single recharger. The brine source can have a significantly larger volume from 1-100× or greater to ensure that the brine source need not be refilled each time a zirconium phosphate is recharged. For a zirconium oxide module having between 220 and 340 g of zirconium oxide loaded with 200 mmols of phosphate, a base source having between 0.5 and 2.0 M sodium hydroxide and a flow rate between 30 and 150 mL/min requires between 1 and 4.0 L of base. The base source can be at least between 1 and 4.0 L in volume. For recharging multiple zirconium oxide modules, a larger base source can be used.

Figure 2A:
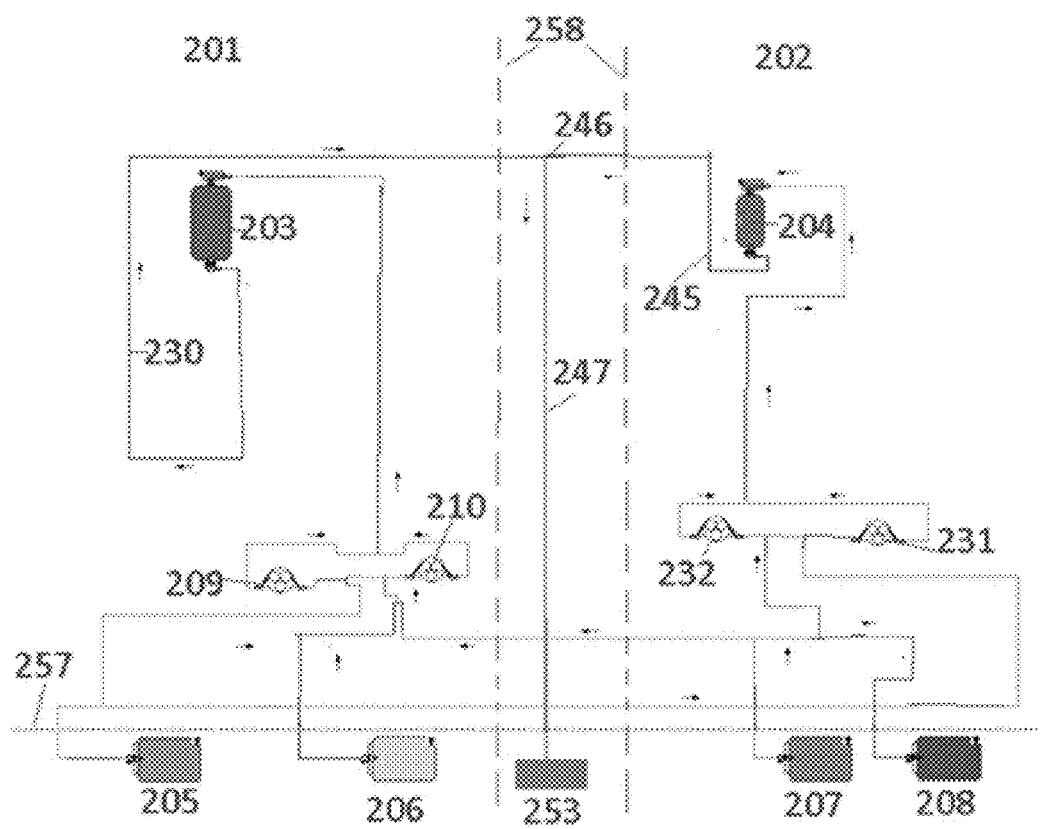
FIG. 2A shows a recharging flow path for recharging zirconium phosphate and zirconium oxide with inline mixing of recharging solutions.
Figure 2B:
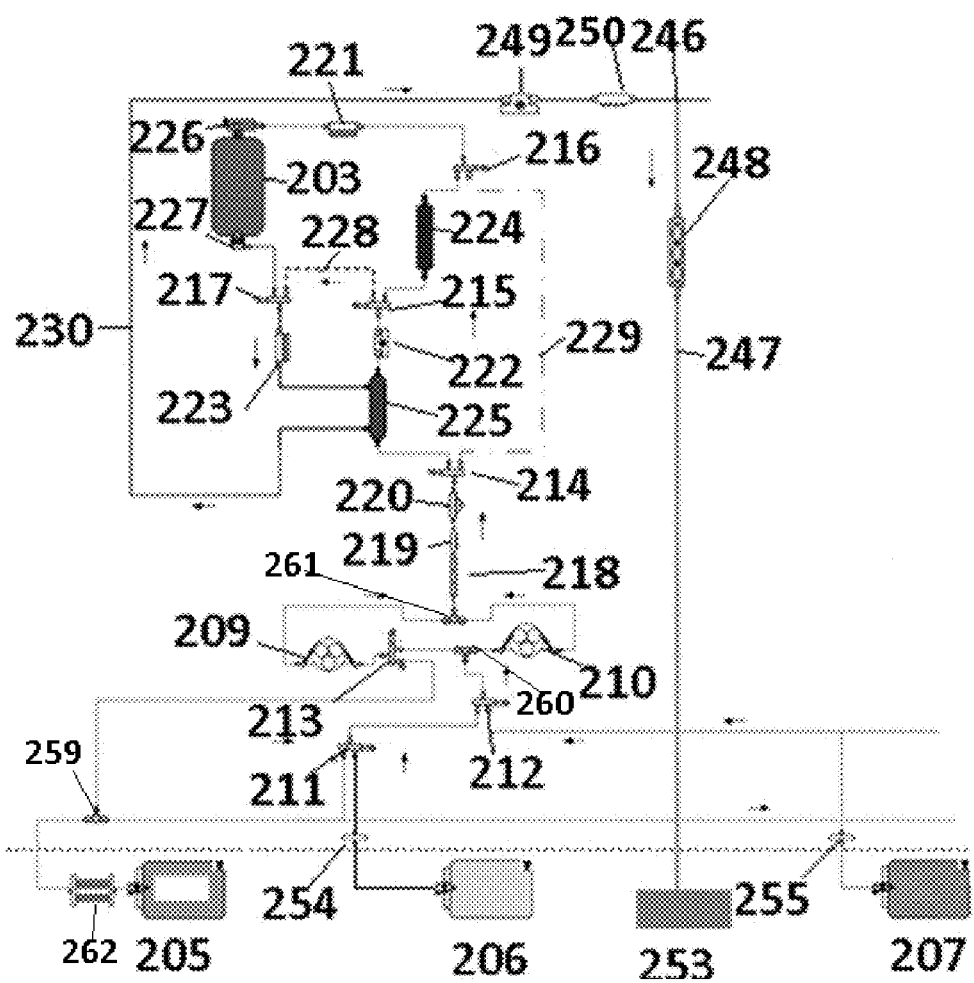
FIG. 2B shows a recharging flow path for recharging zirconium phosphate with inline mixing of recharging solutions and is an exploded right side of FIG. 2A.
Figure 2C:
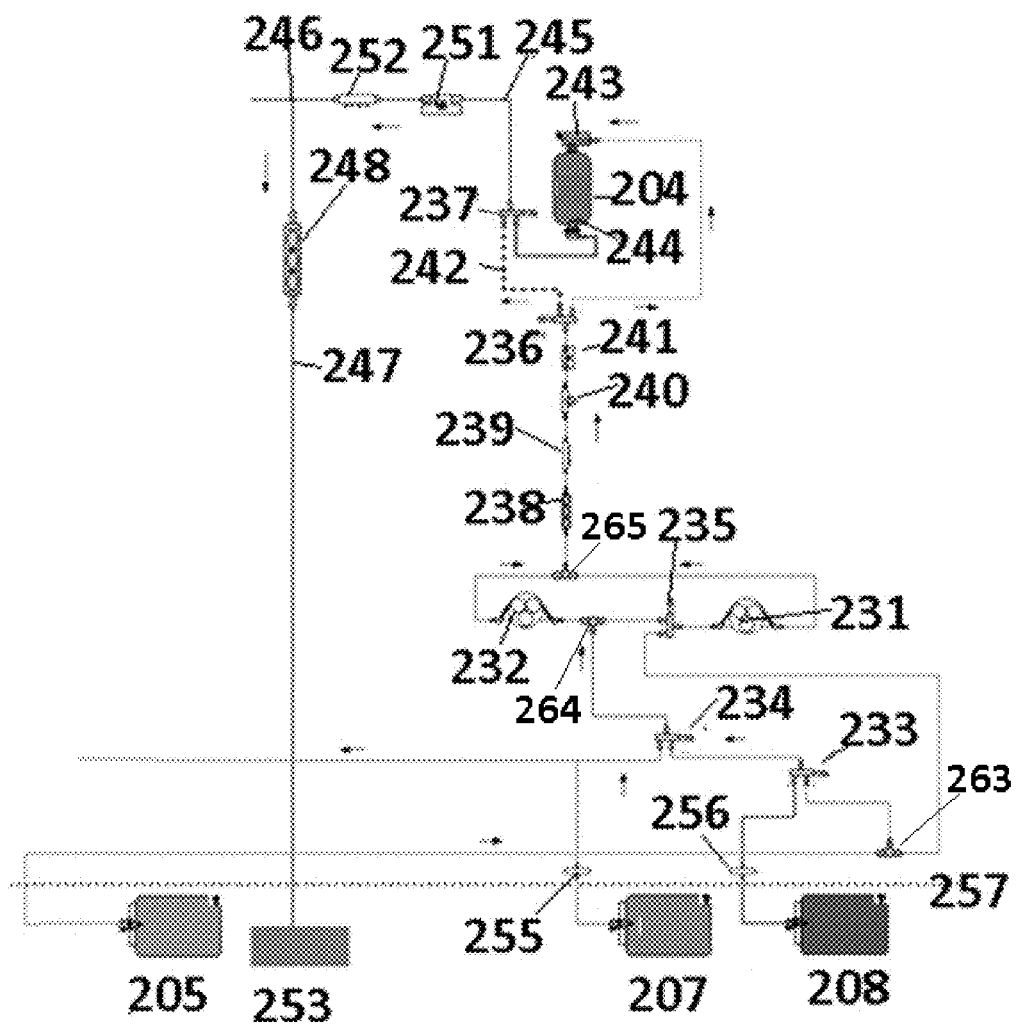
FIG. 2C shows a recharging flow path for recharging zirconium oxide with inline mixing of recharging solutions and is an exploded left side of FIG. 2A.

FIG. 2A is a generalized view of a recharging flow path having a zirconium phosphate recharging flow path 201 containing a zirconium phosphate module 203 and a zirconium oxide recharging flow path 202 containing a zirconium oxide module 204. FIG. 2B illustrates a detailed view of zirconium phosphate recharging flow path 201 on the zirconium phosphate side of line 258, and FIG. 2C illustrates a detailed view of zirconium oxide recharging flow path 202 on the zirconium oxide side of line 258. The valves, pumps and static mixers illustrated in FIGS. 2B and 2C allow for inline mixing of the recharging fluids. In FIG. 2A, the zirconium phosphate recharging flow path 201 and/or zirconium oxide recharging flow path 202 can be simultaneously or independently connected to a water source 205, a brine source 206, a disinfectant source 207, and a base source 208. Because recharging of the zirconium phosphate in a zirconium phosphate module 203 can require water, brine, and disinfectant, and because recharging of zirconium oxide in zirconium oxide module 204 can also require water, base, and disinfectant, the water source, 205, the brine source 206, and the disinfectant source 207 can be jointly connected to the zirconium phosphate recharging flow path 201, and the water source 205, the disinfectant source 207, and the base source 208 can be jointly connected to the zirconium oxide recharging flow path 202.

In FIG. 2A, zirconium phosphate recharging flow path 201 and zirconium oxide recharging flow path 202 can mix chemicals in-line to create the recharging solutions. Any one of disinfectant source 207, brine source 206, and base source 208 can contain solutions having concentrations over the concentration of the components to be used in recharging the reusable modules. Water source 205 can dilute the disinfectant, brine, and base from the fluid sources prior to recharging. In FIG. 2B, zirconium phosphate pump 210 can pump disinfectant into the zirconium phosphate module 203 with in-line mixing of concentrated disinfectant from disinfectant source 207 from valve 212 through junctions 260 and 261 and into static mixer 218. Concurrently, zirconium phosphate pump 209 can pump water through junction 259 and valve 213 and into static mixer 218 from water source 205. Alternatively, the concentrated disinfectant and water can be mixed through fluid line mixing at the junction of the two fluid lines. The zirconium phosphate pumps 209 and 210 can pump a disinfectant solution having a specified concentration and composition to disinfect the zirconium phosphate module 203 via valves 212 and 213. The disinfectant solution can flow from static mixer 218 through valve 214 to valve 216 and then into the zirconium phosphate module 203 through zirconium phosphate module inlet 226. Fluid can exit zirconium phosphate module 203 through zirconium phosphate module outlet 227 into zirconium phosphate effluent line 230. After disinfection of zirconium oxide module 203, zirconium phosphate pumps 209 and 210 can pump water from water source 205 into zirconium phosphate module 203. For example, zirconium phosphate pump 209 can pump water through valve 213 to zirconium phosphate module 203 while zirconium phosphate pump 210 can pump water through valves 211 and 212 to zirconium phosphate module 203. Alternatively, zirconium phosphate pump 209 can pump water through valves 211, 212, and 213 while zirconium phosphate pump 210 pumps water through valves 211 and 212. During recharging, zirconium phosphate pumps 209 and 210 can pump brine through valve 211 to valve 212 from brine source 206 into static mixer 218. If a concentrated brine solution is being used, zirconium phosphate pumps 209 and/or 210 can pump water from water source 205 to static mixer 218 to dilute the brine solution and generate a brine solution having a proper solute concentration for recharging the zirconium phosphate. After pumping brine through the zirconium phosphate module 203, zirconium phosphate pump 209 can pump water through valves 211, 212 and 213 while zirconium phosphate pump 210 can pump water through valve 211 and 212.

The zirconium phosphate recharging flow path 201 of FIG. 2B can have a heater 224 and heat exchanger 225. One or more heat exchangers and one or more heaters can be used. The brine solution can be heated by the heater 224 upstream of the zirconium phosphate module 203. Heat exchanger 225 can utilize the heat from brine exiting the zirconium phosphate module 203 to heat the incoming brine solution upstream of heater 224 to reduce the burden on heater 224. As described, the zirconium phosphate recharging flow path 201 can also have an optional zirconium phosphate bypass line 228 fluidly connecting valve 215 in the zirconium phosphate inlet line to valve 217 in the zirconium phosphate effluent line 230. The zirconium phosphate bypass line 228 can neutralize the zirconium oxide effluent with brine even if the zirconium phosphate module 103 is not being recharged. Zirconium phosphate recharging flow path 201 can have a rinse loop 229 connecting valve 214 upstream of the heater 224 and heat exchanger 225 to valve 216 to bypass heater 224 and heat exchanger 225 to rinse brine out of the zirconium phosphate module 203.

Various sensors can be included in the zirconium phosphate recharging flow path 201 to ensure fluid parameters are within acceptable ranges. In FIG. 2B, conductivity sensor 219 can be placed downstream of static mixer 218 to ensure mixing and specified recharging fluid concentrations. Pressure sensor 220 can measure the fluid pressure and to identify leaks or occlusions. Flow sensor 222 can determine the flow rate of the fluid entering the zirconium phosphate module 203 and be used to control zirconium phosphate pumps 209 and 210. Temperature sensor 221 can determine if the recharging fluid is a proper temperature range upon entering zirconium phosphate module 203 and relay data to a processor (not shown) that can control heater 224. Temperature sensor 223 can determine the temperature of the zirconium phosphate effluent prior to entering heat exchanger 225. Other sensor arrangements, including any number of conductivity, pressure, flow, and temperature sensors can be used.

In FIG. 2C, zirconium oxide pump 232 can pump disinfectant from disinfectant source 207 through valve 234 and into static mixer 238 to disinfect the zirconium oxide module 204 in zirconium oxide recharging flow path 202. Zirconium oxide pump 231 can pump water from water source 205 through valve 235 to static mixer 238 to dilute the disinfectant from disinfectant source 207 to provide in-line mixing of the disinfectant solution. The diluted disinfectant can then be pumped through valve 236 to zirconium oxide module inlet 243 and into zirconium oxide module 204. Effluent from the zirconium oxide module 204 can exit through zirconium oxide module outlet 244 and into zirconium oxide effluent line 245. After disinfection, the disinfectant can be rinsed from the zirconium oxide module 204 by pumping water from water source 205 through valve 235 to zirconium oxide module 204 by zirconium oxide pump 231 while zirconium oxide pump 232 pumps water through valves 233 and 234 to zirconium oxide module 204. Alternatively, zirconium oxide pump 231 can pump water through valves 233, 234, and 231, while zirconium oxide pump 232 pumps water through valves 233 and 234. To recharge zirconium oxide module 204, zirconium oxide pump 232 can pump base from base source 208 through valves 233 and 234 through junctions 264 and 265 to static mixer 238. Water from water source 205 can be pumped by zirconium oxide pump 231 through junctions 263 and 265 into static mixer 238 to dilute the base by in-line mixing. Alternatively, the water and base can be mixed through fluid line mixing at the junction of the two fluid lines. Alternatively, the base can be pre-set using specified amounts of base in pre-packaged packets or containers. Diluted base can flow through the zirconium oxide recharging flow path 202 and through zirconium oxide module 204. The zirconium oxide module 204 can be rinsed any numbers of times, as needed, by introducing water from water source 205 to the zirconium oxide module 204. The zirconium oxide recharging flow path 202 can also have a zirconium oxide bypass line 242 that fluidly connects valve 236 to valve 237 in the zirconium oxide effluent line 245 to bypass zirconium oxide module 204. In this way, zirconium phosphate effluent can be neutralized with a base solution even if the zirconium oxide module 204 is not being recharged. A heater and heat exchanger (not shown) can be positioned in the zirconium oxide recharging flow path 202 to heat fluids prior to entering zirconium oxide module 204. A zirconium oxide rinse loop (not shown) can also be included to bypass the heater and heat exchanger. Similarly, the zirconium oxide recharging flow path 202 can also have sensors for measurement and control over the recharging process. In FIG. 2C, a conductivity sensor 239 can be placed downstream of static mixer 238 to ensure that diluted recharging solutions have a desired concentration. Pressure sensor 240 can detect the pressure in the zirconium oxide recharging flow path 202 to detect leaks or occlusions. Flow sensor 241 can detect the flow rate of fluid in the zirconium oxide recharging flow path 202 and can be used to control zirconium oxide pumps 231 and 232.

As shown in FIG. 2A, the present invention can provide in-line neutralization of the effluent from each of the zirconium phosphate recharging flow path 201 and zirconium oxide recharging flow path 202. The zirconium phosphate effluent line 230 can be fluidly connected to zirconium oxide effluent line 245 at effluent line junction 246 and fluidly connected to drain line 247. As shown in FIGS. 2B and 2C, a static mixer 248 can be positioned at or downstream of the effluent line junction 246 to ensure mixing of the effluents from the zirconium phosphate recharging flow path 201 and zirconium oxide recharging flow path 202. The combined effluent can be conveyed through the drain line 247 to drain 253, or to a common waste reservoir (not shown), or to separate waste reservoirs. A conductivity sensor 250 as shown in FIG. 2B in zirconium phosphate effluent line 230 and a conductivity sensor 252 as shown in FIG. 2C in zirconium oxide effluent line 245 can determine the composition of the effluents. Flow sensor 249 in zirconium phosphate effluent line 230 of FIG. 2B and flow sensor 251 in zirconium oxide effluent line 245 of FIG. 2C can be used simultaneously or independently to measure the flow rates of each of the effluents. Determining the composition of the effluent fluids as well as the respective flow rates using one or more sensors described can monitor the system function and ensure that the combined effluent in drain line 247 is safe for disposal or storage.

Brine source 206, disinfectant source 207, and base source 208 can have filter 254, filter 255, and filter 256, respectively to remove particulate matter prior to entering zirconium phosphate recharging flow path 201 or zirconium oxide recharging flow path 202. The filters can also act as inline mixers to mix the solutions. Water source 205 can have microbial filter 262 to remove microbes from the water. Brine source 206, disinfectant source 207, and base source 208 can be housed outside of a recharger housing denoted by line 257. The brine solution, disinfectant solution, and base solution can be generated through in-line mixing as described. Alternatively, pre-mixed solutions, concentrates, or infusates can be introduced into brine source 206, disinfectant source 207, and base source 208 and delivered to zirconium phosphate recharging flow path 201 or zirconium oxide recharging flow path 202. For example, the brine solution in brine source 206 can be pre-mixed or provide in pre-packaged amounts in the proper concentrations and introduced into brine source 206, disinfectant source 207, and base source 208.

In-line mixing can provide higher concentrations of solutes, lower fluid volumes required by the system, and physically smaller fluid reservoirs. The fluids should have suitable concentrations for use in the zirconium phosphate recharging flow path 201 or zirconium oxide recharging flow path 202. An initially high source of disinfectant, such as peracetic acid, can be used in a concentration of between 20% and 40%. The zirconium phosphate recharging flow path 201 of FIG. 2B can dilute the peracetic acid or other disinfectant source by a factor of 20:1 to 40:1 to generate an acidic recharging solution having a concentration between 0.5% and 2%. The initial disinfectant concentration can be any concentration greater than 1%. Similarly, the base solution can be sodium hydroxide having an initial concentration between 14M and 22M. The zirconium oxide recharging flow path 202 of FIG. 2C can dilute the base solution by 18:1 to 22:1 to generate a base solution having a concentration between 0.8 and 1.0 M. The initial base solution concentration can be any concentration greater than or equal to 0.5 M. The brine solution can also be diluted in-line to generate a brine solution having a proper recharging concentration. One example is a brine concentrate at 4.90M NaCl, 0.40M sodium acetate and 0.26M acetic acid diluted to 3.7M NaCl, 0.30M sodium acetate, and 0.20M acetic acid. The brine source 206 of FIG. 2A can be one or more reservoirs. For example, an acetic acid source, a sodium acetate source and a sodium chloride source can each be connected in place of single brine source 206. Alternatively, an acetic acid source, a base source, and a sodium chloride source can be connected in place of the single brine source 206 with mixing of the base and acetic acid to generate the sodium acetate. The individual components can be added to the zirconium phosphate recharging flow path 201 in the proper ratios to generate the recharging brine.

The chemicals used in the recharging process can be packaged and shipped in any form. The chemicals can be packaged and shipped as solutions, either in proper concentrations for recharging or with higher concentrations for inline mixing. In any embodiment, the chemicals may be packaged and shipped in pure form, such as 100% acetic acid or solid sodium chloride, sodium acetate, or sodium hydroxide.

Figure 3:
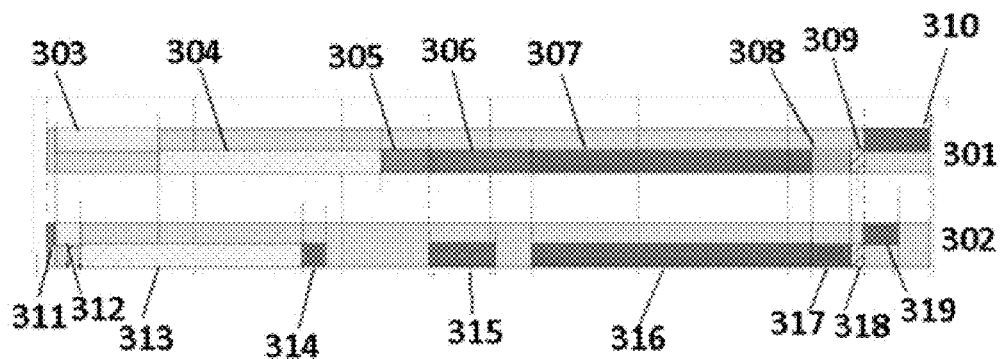
FIG. 3 shows a timeline for concurrent recharging of zirconium oxide and zirconium phosphate.

FIG. 3 illustrates a non-limiting example of a timeline that can be used for concurrent or separate recharging of zirconium phosphate and zirconium oxide. Timeline 301 shows recharging zirconium phosphate and timeline 302 shows recharging zirconium oxide. As illustrated in timeline 301, the zirconium phosphate recharging process can begin by introducing a disinfectant, such as peracetic acid, into the zirconium phosphate module, shown as step 303. The time necessary to fill the zirconium phosphate module with the disinfectant can depend on the flow rate of the disinfectant solution and the volume of the zirconium phosphate module. The disinfectant can be delivered to the zirconium phosphate module in step 303 at a flow rate of between 100 and 500 mL/min, which can fill a zirconium phosphate module in a time of between 5-10 minutes. Longer or shorter flushing times can be used depending on the need. After filling the zirconium phosphate with the disinfectant solution, the disinfectant solution can be held in the zirconium phosphate module to ensure disinfecting of the zirconium phosphate module in step 304. In any embodiment, the disinfectant can be held in the zirconium phosphate module for any length of time sufficient to disinfect the zirconium phosphate module, including between 5 and 20 minutes. The temperature of the disinfectant can be determined with a temperature sensor, and the hold time adjusted as necessary. For example, if the disinfectant temperature is 22° C., the hold time can be 5 minutes. The disinfectant can also be heated to minimize the necessary hold time by heating the disinfectant to room temperature if necessary. During the hold time, the disinfectant flow can be stopped or reduced to a low flow condition, such as 5 to 75 ml/min. Holding the disinfectant in the module can build up pressure in the module, requiring periodic venting. To maintain the volume after venting, during which some fluid may leak, the disinfectant can be pumped into the module at a low flow rate during the venting. Alternatively, during the hold time, the disinfectant flow rate can be set to between 5 and 75 ml/min to prevent pressure buildup while maintaining fluid volume in the modules. The disinfectant solution can then be flushed from the zirconium phosphate module in step 305 by pumping water through the zirconium phosphate module. The water can flow through the zirconium phosphate module at a specified rate. A higher flow rate of the water in step 305 will cause a quicker flush time. The water can be pumped through the zirconium phosphate module at a rate of between 300 and 500 mL/min. Depending on the size of the zirconium phosphate module, the zirconium phosphate module can be flushed in about 5-10 minutes. As described, the system can utilize one or more sensors, such as pH sensors or conductivity sensors in the zirconium phosphate effluent lines to determine if disinfectant is fully flushed in step 305. After flushing the disinfectant from the zirconium phosphate module in step 305, brine solution can be pumped through the zirconium phosphate module to recharge the zirconium phosphate module starting in step 306. The brine solution can be pumped through the zirconium phosphate module in step 306 at any rate. One of skill in the art will understand that a higher flow rate of brine solution may decrease the time necessary to recharge the zirconium phosphate, but may also decrease the efficiency of the process, resulting in the need for additional brine. Conductivity or pH sensors can be used to determine if the zirconium phosphate module has been fully filled with brine.

The brine flow rate can be set to any flow rate, including between 150 and 250 mL/min. Depending on the size of the zirconium phosphate module, between 5 and 10 minutes may be needed for brine to reach the sensors in the zirconium phosphate effluent line. Once brine has reached the sensors in the effluent line, the brine can flow through the zirconium phosphate module in step 307 until recharging is complete. Recharging time can vary based on the flow rate of the brine solution, the concentration of the brine solution, and the temperature of the brine solution. For example, the brine solution can be heated during the recharging process between 65° C. and 95° C. Recharging of zirconium phosphate can be more efficient at elevated temperatures. Conductivity sensors can determine if step 308 has been completed by detecting the conducting of the fluid in the zirconium phosphate effluent line. If the conductivity of the effluent matches the conductivity of the brine, then no additional ions from the brine are being exchanged onto the zirconium phosphate, and recharging is complete. For example, steps 308, 309, and 310 represent brine solution being flushed from the zirconium phosphate module with water. Flushing can continue through step 310 until the conductivity sensors in the zirconium phosphate effluent line determine no additional brine is being removed from the zirconium phosphate module.

As depicted in timeline 302, zirconium oxide can be recharged concurrently or independently of zirconium phosphate. In step 311, zirconium oxide recharging begins by rinsing the zirconium oxide module with water. The water rinse can flush leftover dialysate bicarbonate or any sodium hydroxide from the flow loop, which may react violently with acid necessary for disinfection. After flushing the zirconium oxide module with water in step 311, disinfectant solution can be delivered to disinfect the module in step 312. The time necessary to fill the zirconium oxide module with disinfectant depends on the size of the zirconium oxide module and the flow rate of the disinfectant. Because less zirconium oxide is needed for dialysis than zirconium phosphate, the zirconium oxide module may be smaller than the zirconium phosphate module, and therefore fill faster in step 312 as compared to the zirconium phosphate module in step 303. Upon filling, the disinfectant can be sequestered in the zirconium oxide module to allow for disinfection in step 313. The disinfectant can be held in the zirconium oxide module for any length of time, including between 5 and 20 minutes. The temperature of the disinfectant can be determined with a temperature sensor, and a hold time adjusted as necessary. For example, if the disinfectant temperature is 22° C., the hold time can be 5 minutes. The disinfectant can also be heated to minimize the necessary hold time. Upon disinfection, the disinfectant can be flushed from the zirconium oxide module in step 314.

In step 315 the base solution flows through the zirconium oxide module to recharge the zirconium oxide. Step 315 continues until a basic solution is detected in the zirconium oxide effluent line. During simultaneous recharging, the basic effluent from the zirconium oxide recharging flow path neutralizes the acidic effluent from the zirconium phosphate recharging flow path. Once a basic effluent is detected in step 315, the zirconium oxide recharging process can be halted until the acid brine is detected in the effluent of the zirconium phosphate module in step 306, which may occur later due to size differences of the zirconium phosphate and zirconium oxide modules. After the acidic effluent is detected in the zirconium phosphate module, shown as step 306, the base can continue to flow through the zirconium oxide module in step 316. The flow rate of the base solution in step 316 can be any suitable rate. For example, the flow rate of the base solution can be between 30 and 150 mL/min. To ensure neutralization, the flow rate of the base in step 316 can depend on the flow rate of the brine in step 307. As described, the base and effluent are each brought to a point equidistant to a junction between the zirconium phosphate and zirconium oxide effluent lines. Based on the conductivity of each effluent, the pumping is restarted at a ratio of speed that is needed for neutralization. The ratio could be 1:1 or any other ratio. Although described as using a conductivity sensor, the system can alternatively use a pH sensor or a combination of pH and conductivity sensors. A neutralization ratio can be calculated based on the relative pH, buffer capacity, and concentration of the zirconium phosphate effluent and zirconium oxide effluent. For example, a neutralization ratio of 1.5:1 means that 1.5 liters of the zirconium phosphate effluent will be required to fully neutralize one liter of zirconium oxide effluent. The flow rate of the base in step 316 can be set to half the flow rate of the brine solution, allowing full neutralization of both solutions. For example, the flow rate of the base in step 316 can be between 75 and 125 mL/min if the neutralization ratio is 1.5:1 and the brine flow rate is between 150 and 250 mL/min.

After the brine solution is detected in the effluent of the zirconium phosphate and the flushing of the brine begins in step 308, the base solution can pass through the zirconium oxide module, shown as step 317 until the brine is mostly or fully flushed from the zirconium phosphate module, shown as step 309. At this point, the base solution can be flushed from the zirconium oxide module, shown as step 318. After confirming that the base has been flushed from the zirconium oxide module, flushing is completed in step 319.

One of skill in the art will understand that the times and flow rates described in FIG. 3 can be altered within the scope of the invention. Higher flow rates can cause faster recharging of the modules. Times can be decreased by using more concentrated solutions, but may decrease efficiency. Specified concentrations, flow rates, and times can be set per the needs of the user, taking into account the cost of chemicals and need for fast recharging. The times and flow rates shown in zirconium oxide recharging timeline 302 can also be altered to reduce idle time. For example, the flow rate of the base solution in step 315 can be slowed down to reduce the time gap between steps 315 and 316. If a single sorbent module is being recharged independently, or if a common waste reservoir is used for the zirconium phosphate and zirconium oxide recharging flow paths either inside or outside of the recharger—the times and flow rates shown in FIG. 3 can be adjusted. Synchronizing the zirconium phosphate timeline 301 with the zirconium oxide timeline 302 is unnecessary because effluent is no longer neutralized in-line.

The zirconium oxide and zirconium phosphate sorbent modules can be recharged and reused any number of times. Alternatively, the sorbent modules may have a defined useful life, including a maximum number of recharge and reuse cycles. When a sorbent module reaches the end of the sorbent module's useful life, the sorbent module can be recycled or disposed of. A disinfection only cycle can disinfect the sorbent modules for safe disposal and/or recycling at the end of the sorbent module's useful life. In a disinfection only cycle, the disinfectant can be pumped into the sorbent module as described but the other recharge solutions would not be used. After disinfection, and optionally rinsing of the sorbent module, the sorbent module can be disposed or recycled safely.

Figure 4:
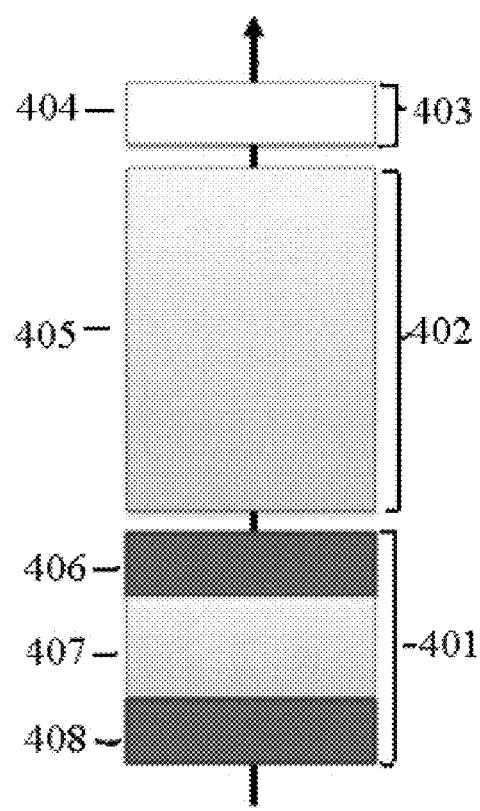
FIG. 4 shows material layers in a module sorbent cartridge including reusable modules.

A non-limiting embodiment of a reusable sorbent cartridge having modules that can be separated and recharged by systems and methods of the present invention is in FIG. 4. The sorbent cartridge can be separated into reusable modules to facilitate recharging of one or more sorbent materials. In FIG. 4, the sorbent cartridge has a first sorbent module 401, a second sorbent module 402, and a third sorbent module 403. The first module 401 can have a layer of activated carbon 408, a layer of alumina and urease 407, and a second layer of activated carbon 406. The activated carbon can remove many non-ionic solutes from the dialysate. The urease catalyzes the conversion of urea in the dialysate into ammonium ions. The alumina can serve as a support for the urease. The second layer of activated carbon 406 can capture any urease that migrates out of alumina and urease layer 407 prior to exiting the first module 401. The first module 401 can be a single use module, or can be a multiple use module with replenishment of the urease. The second module 402 can have zirconium phosphate 405. After dialysis, zirconium phosphate 405 will contain bound potassium, calcium, magnesium, and ammonium ions, which can be replaced with sodium and hydrogen ions by the recharging process described herein. Third module 403 can contain zirconium oxide 404. After use, the zirconium oxide 404 will contain bound phosphate, fluoride and other anions, which can be replaced with hydroxide anions through the recharging process described herein. The direction of flow of dialysate through the sorbent cartridge is shown by the arrow in FIG. 4. The recharging solutions can also flow through the reusable sorbent modules in an opposite direction to improve the efficiency of the recharging process.

Figure 5:
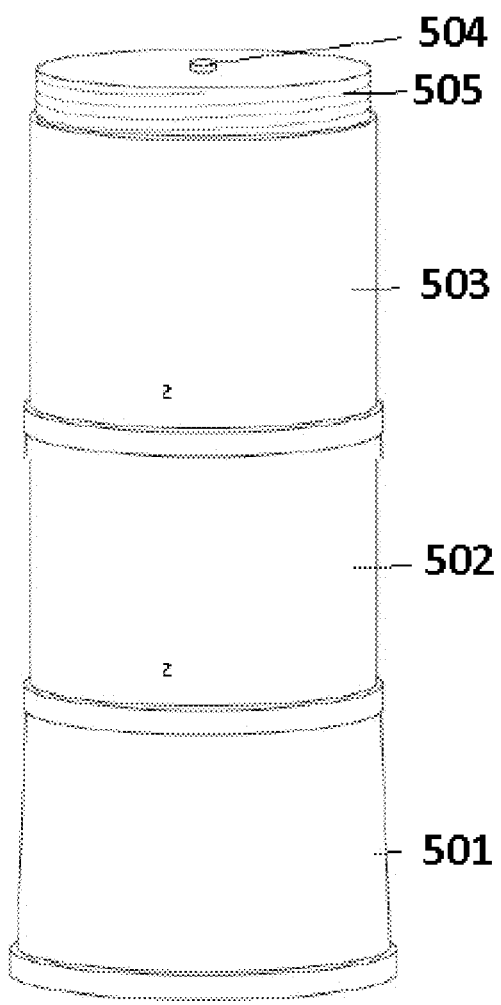
FIG. 5 shows multiple sorbent modules connected together to form a sorbent cartridge.

FIG. 5 illustrates another non-limiting example of a modular sorbent cartridge that can be used in the recharging process described herein. The modular sorbent cartridge can be separated into discrete modules including a first module 501, a second module 502, and a third module 503 connected together to form a sorbent cartridge. The first module 501 can contain activated carbon, urease, and alumina; the second module 502 can contain zirconium phosphate; and the third module 503 can contain zirconium oxide. One of skill in the art will understand that the modular sorbent cartridge illustrated in FIG. 5 is for illustrative purposes only, and modifications to the sorbent cartridge can be made within the scope of the invention. Alternatively, the sorbent modules can be independent with fluid lines connecting each of the sorbent modules for dialysis. During dialysis, dialysate can enter the sorbent cartridge through the bottom of first module 501, travel through modules 501, 502, and 503, and exit through fluid outlet 504. The fluid outlet 504 can connect to the rest of the dialysate flow path. Threaded portion 505 on module 503 can be used in connecting modules to each other, to the dialysate flow path, or to the recharger as described herein. The threaded portion 505 can be included on any of the sorbent modules. Other connection types suitable for secured fluid connection in dialysis known in the art is contemplated by the invention. For example, fluid lines can be clamped directly onto fluid outlet 504. After dialysis, a user can disconnect the sorbent modules for disposal of single use modules and for recharging of the reusable modules.

Figure 6:
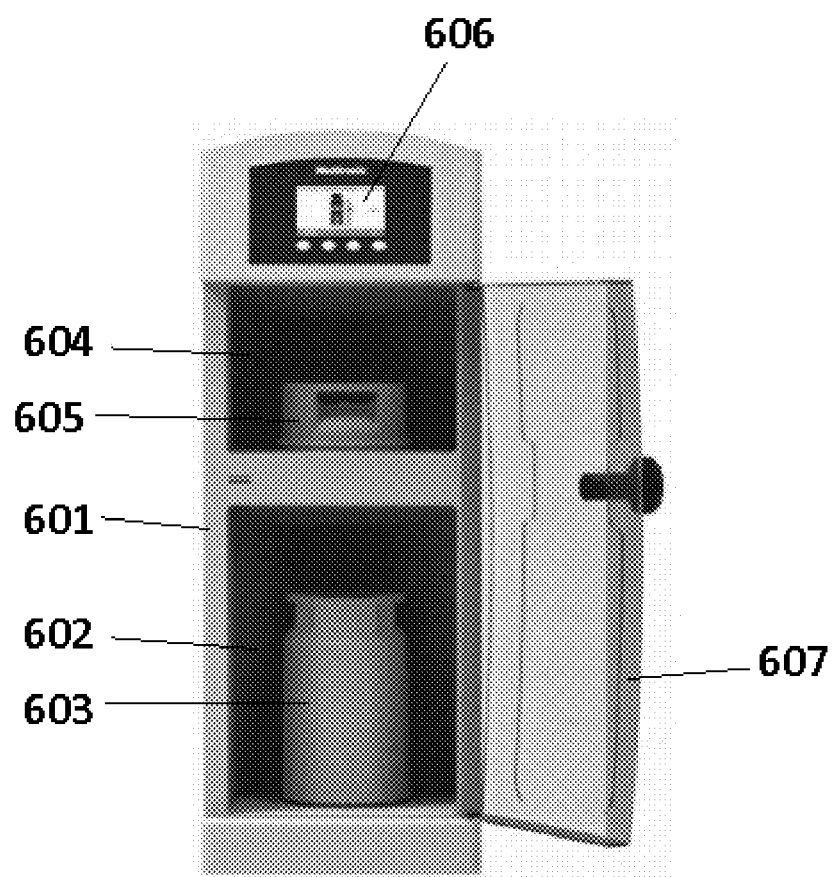
FIG. 6 shows a recharger for recharging zirconium phosphate and zirconium oxide sorbent modules.

FIG. 6 illustrates a non-limiting embodiment of a recharger 601 configured for recharging zirconium phosphate and zirconium oxide modules. The recharger 601 can have a zirconium phosphate receiving compartment 602 configured to hold a zirconium phosphate sorbent module 603. The recharger 601 can also have a zirconium oxide receiving compartment 604 configured to hold a zirconium oxide sorbent module 605. Fluid connectors (not shown in FIG. 6) can provide fluid connection to the fluid sources described herein. One or more fluid sources can be housed within the recharger 601 or outside of the recharger 601 with fluid connectors connecting the fluid sources to the recharging flow paths. Fluid sources placed external to the recharger 601 can result in a compact recharger 601. The recharger 601 can have a door 607 which can prevent access to the reusable modules during operation. The recharger 601 can also have a user interface 606. The user interface 606 can start or control the recharging process by the user. Further, the user interface 606 can provide the status of the recharging process to the user such as the times to completion for each recharging step in FIG. 3. User interface 606 can also provide alert messages if any problems are detected during recharging, such as leaks, occlusions, pump failures, or mismatched chemicals. Rechargers with any number of receiving compartments for recharging any number or combination of zirconium oxide and/or zirconium phosphate sorbent modules can be constructed. For example, a recharger with two zirconium phosphate receiving compartments and two zirconium oxide receiving compartments can be similarly constructed. The rechargers can have 1, 2, 3, 4, 5, 6, or more receiving compartments, each capable of receiving zirconium oxide or zirconium phosphate sorbent modules.

Figure 7:
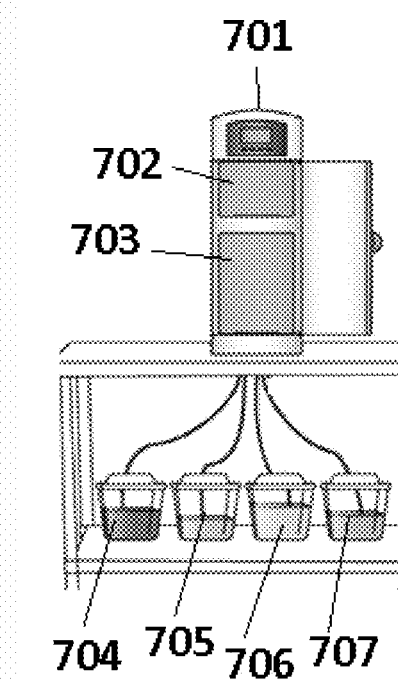
FIG. 7 shows a recharger fluidly connected to external fluid sources.

FIG. 7 illustrates a non-limiting embodiment of a recharger set up for recharging zirconium oxide and zirconium phosphate. The recharger 701 can have a zirconium phosphate receiving compartment 702 and a zirconium oxide receiving compartment 703. External fluid sources such as water source 704, brine source 705, disinfectant source 706, and base source 707 can be fluidly connected to the recharger 701. The pumps, valves, fluid lines, and other components described in FIGS. 1-2 can be fluidly connected to the fluid sources inside recharger 701.

The rechargers can be used in any setting, including a clinic, at home, or in a mobile setting. In any setting, the rechargers can use a water tank or any other source of potable or deionized water. For use in a mobile setting, vans or trucks can carry the rechargers, the disinfectant source, the brine solution, the base solution, and optionally the water, to a location for recharging. For at home use, the brine solution, disinfectant solution, base solution, and optionally the water, may be prepackaged and shipped to a patient. The patient can connect each of the sources to the recharger to allow recharging and reuse of the sorbent modules in dialysis. As described, the rechargers can provide for inline mixing of chemicals, reducing the amount of chemicals required to be moved for use in a mobile setting. Inline mixing of chemicals allows for a smaller amount of concentrated solutions to be moved to a location in a mobile or at home setting, and water from a local water source, such as municipal drinking water, can be used to dilute the disinfectant, base, and/or brine inline. Alternatively, a deionized or purified water source can be provided in a mobile setting. Effluent from the sorbent modules can be collected and neutralized inline for immediate disposal in any drain, or can be collected for later neutralization and disposal offline. The ability to neutralize and dispose of the combined effluents in a drain allow for easier use in an at home or mobile setting, without the need for large waste reservoirs and further treatment.

Figure 8:
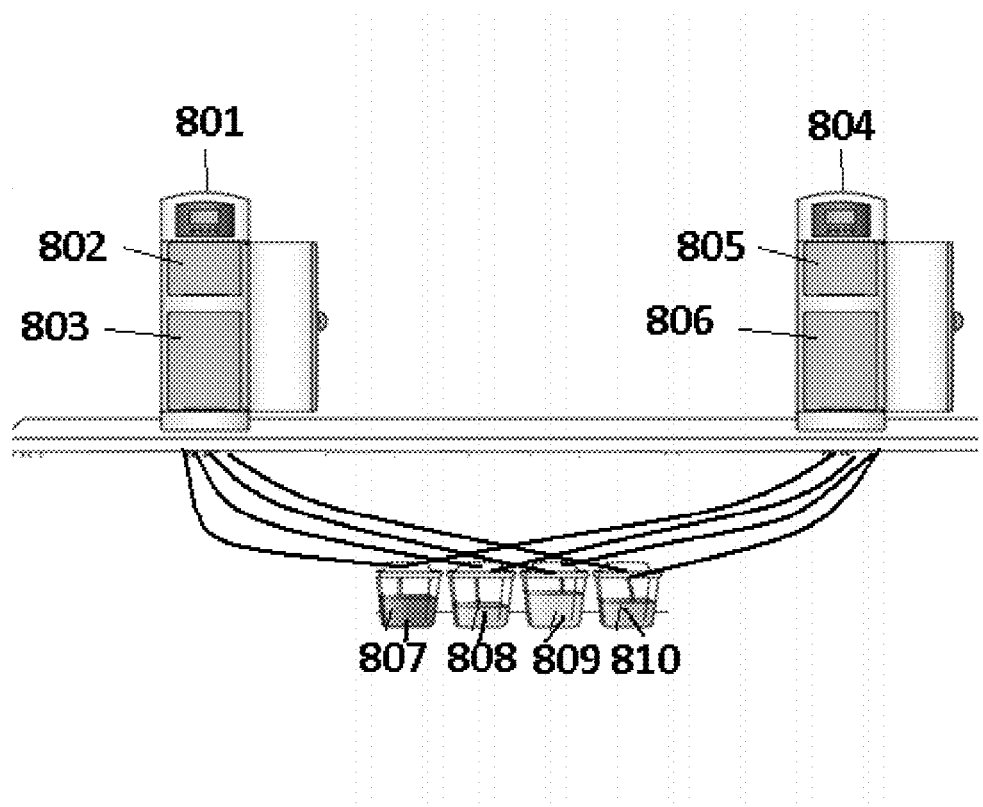
FIG. 8 shows multiple rechargers fluidly connected to a single set of fluid sources.

In FIG. 8, multiple rechargers can be connected together to share fluid sources and to decrease space requirements and costs. A first recharger 801 having a zirconium phosphate receiving compartment 803 and zirconium oxide receiving compartment 802 can be fluidly connected to water source 807, brine source 808, disinfectant source 809, and base source 810. A second recharger 804 can also be fluidly connected to water source 807, brine source 808, disinfectant source 809, and base source 810. Any number of rechargers can be connected to a common set of fluid sources, including 2, 3, 4, 5, 6 or more rechargers each fluidly connected to a single set of fluid sources and a single set of waste reservoirs. Connecting multiple rechargers to a single set of fluid sources saves space and materials and simplified recharging multiple sets of reusable modules in a clinic or hospital setting. Each of the connected rechargers can have separate heaters for heating the brine and/or disinfectant solutions, or centralized heaters can be included, with centralized heating of the shared solutions.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A recharging flow path, comprising:
a zirconium phosphate recharging flow path and a zirconium oxide recharging flow path;
the zirconium phosphate recharging flow path comprising:
i) a water source, a disinfectant source, and a brine source;
ii) a zirconium phosphate module inlet and a zirconium phosphate module outlet; wherein the zirconium phosphate module inlet and the zirconium phosphate module outlet are fluidly connectable to a sorbent module containing zirconium phosphate;
iii) at least one zirconium phosphate pump for conveying fluid from the water source, the disinfectant source, and the brine source to the zirconium phosphate module inlet; and
iv) a zirconium phosphate effluent line in fluid connection to the zirconium phosphate module outlet;
the zirconium oxide recharging flow path comprising:
i) the water source, the disinfectant source, and a base source;
ii) a zirconium oxide module inlet and a zirconium oxide module outlet; wherein the zirconium oxide module inlet and the zirconium oxide module outlet are fluidly connectable to a sorbent module containing zirconium oxide;
iii) at least one zirconium oxide pump for conveying fluid from the water source, the disinfectant source, and the base source to the zirconium oxide module inlet; and
iv) a zirconium oxide effluent line in fluid connection to the zirconium oxide module outlet.

2. The recharging flow path of claim 1, wherein either or both of the zirconium phosphate recharging flow path and the zirconium oxide recharging flow path comprise at least two pumps.

3. The recharging flow path of claim 1, wherein the zirconium phosphate effluent line is fluidly connected to the zirconium oxide effluent line at an effluent line junction.

4. The recharging flow path of claim 3, further comprising a static mixer downstream of the effluent line junction.

5. The recharging flow path of claim 4, further comprising a drain line fluidly connected to the effluent line junction, wherein the drain line is fluidly connected to a drain downstream of the static mixer.

6. The recharging flow path of claim 1, wherein the zirconium phosphate effluent line is fluidly connected to a first waste reservoir; and wherein the zirconium oxide effluent line is fluidly connected to a second waste reservoir.

7. The recharging flow path of claim 1, further comprising a common reservoir, said common reservoir being fluidly connected to the zirconium phosphate effluent line and zirconium oxide effluent line.

8. The recharging flow path of claim 1, further comprising either or both of:
a heater positioned in the zirconium phosphate recharging flow path upstream of the zirconium phosphate module inlet; or
a heater positioned in the zirconium oxide recharging flow path upstream of the zirconium oxide module inlet.

9. The recharging flow path of claim 8, further comprising a heat exchanger; wherein the heat exchanger comprises at least a first chamber and a second chamber; and wherein either or both of:
the first chamber is positioned in the zirconium phosphate recharging flow path upstream of the heater; and the second chamber is positioned in the zirconium phosphate effluent line; or
the first chamber is positioned in the zirconium oxide recharging flow path upstream of the heater; and wherein the second chamber is positioned in the zirconium oxide effluent line.

10. The recharging flow path of claim 9, wherein either or both of the zirconium phosphate recharging flow path or zirconium oxide recharging flow path further comprise a rinse loop; wherein the rinse loop is fluidly connected to a first valve positioned in the zirconium phosphate recharging flow path upstream of the heater and heat exchanger connected to a second valve positioned in the zirconium phosphate recharging flow path downstream of the heater and heat exchanger and upstream of the zirconium phosphate module inlet; or wherein the rinse loop is fluidly connected to a first valve positioned in the zirconium oxide recharging flow path upstream of the heater and heat exchanger and a second valve positioned in the zirconium oxide recharging flow path downstream of the heater and heat exchanger and upstream of the zirconium oxide module inlet.

11. The recharging flow path of claim 1, further comprising either or both of a zirconium phosphate bypass line and a zirconium oxide bypass line; wherein the zirconium phosphate bypass line fluidly connects the zirconium phosphate recharging flow path at a position upstream of the zirconium phosphate module inlet to the zirconium phosphate effluent line; and wherein the zirconium oxide bypass line fluidly connects the zirconium oxide recharging flow path at a position upstream of the zirconium oxide module inlet to the zirconium oxide effluent line.

12. The recharging flow path of claim 3, further comprising a first sensor positioned in the zirconium phosphate effluent line and a second sensor positioned in the zirconium oxide effluent line.

13. The recharging flow path of claim 1, further comprising a first sensor in the zirconium phosphate recharging flow path and a second sensor in the zirconium oxide recharging flow path.

14. The recharging flow path of claim 13, further comprising:
a first zirconium phosphate pump and a second zirconium phosphate pump; wherein the water source is fluidly connected to the zirconium phosphate recharging flow path through a first valve;
wherein either or both of the disinfectant source and brine source is fluidly connected to the zirconium phosphate recharging flow path through a second valve;
the first zirconium phosphate pump positioned in the zirconium phosphate recharging flow path downstream of the first valve and upstream of a static mixer; and the second zirconium phosphate pump positioned in the zirconium phosphate recharging flow path downstream of the second valve and upstream of the static mixer.

15. The recharging flow path of claim 14, wherein the first sensor is positioned downstream of the static mixer.

16. The recharging flow path of claim 13, further comprising:
a first zirconium oxide pump and a second zirconium oxide pump; wherein the water source is fluidly connected to the zirconium oxide recharging flow path through a first valve;
wherein the disinfectant source and the base source are fluidly connected to the zirconium oxide recharging flow path through a second valve;
wherein the first zirconium oxide pump is positioned in the zirconium oxide recharging flow path downstream of the first valve and upstream of a static mixer; and the second zirconium oxide pump is positioned in the zirconium oxide recharging flow path downstream of the second valve and upstream of the static mixer;
wherein the second sensor is positioned downstream of the static mixer.

17. The recharging flow path of claim 1, wherein at least one of the water source, disinfectant source, brine source, and base source is external to a recharger housing.

18. The recharging flow path of claim 17, wherein at least one of the water source, disinfectant source, brine source, and base source are fluidly connected to a second recharging flow path.

19. The recharging flow path of claim 1, wherein the disinfectant source is a peracetic acid solution having a concentration in a range between 0.5% and 2% of peracetic acid in water.

20. The recharging flow path of claim 1, wherein the base source is a sodium hydroxide solution having a concentration greater than 2% of sodium hydroxide in water.

* * * * *